United States Patent
Schlaepfer et al.

(10) Patent No.: US 9,763,702 B2
(45) Date of Patent: Sep. 19, 2017

(54) BONE FIXATION ASSEMBLY

(71) Applicant: DePuy Synthes Products, Inc, Raynham, MA (US)

(72) Inventors: Fridolin Schlaepfer, Hoelstein (CH); Martin Schnider, Subingen (CH); Helmut Rutschmann, Klettgau (DE)

(73) Assignee: DePuy Synthes Products, Inc., Raynham, MA (US)

( * ) Notice: Subject to any disclaimer, the term of this patent is extended or adjusted under 35 U.S.C. 154(b) by 318 days.

(21) Appl. No.: 14/081,117

(22) Filed: Nov. 15, 2013

(65) Prior Publication Data
US 2014/0142634 A1    May 22, 2014

Related U.S. Application Data

(60) Provisional application No. 61/727,290, filed on Nov. 16, 2012, provisional application No. 61/731,772, filed on Nov. 30, 2012.

(51) Int. Cl.
*A61B 17/70*    (2006.01)

(52) U.S. Cl.
CPC ........ *A61B 17/704* (2013.01); *A61B 17/7037* (2013.01); *F04C 2270/0421* (2013.01); *Y10T 29/49826* (2015.01)

(58) Field of Classification Search
CPC .................................. A61B 17/7032–17/7037
See application file for complete search history.

(56) References Cited

U.S. PATENT DOCUMENTS

| | | | |
|---|---|---|---|
| 3,865,105 | A | 2/1975 | Lode |
| 4,411,259 | A | 10/1983 | Drummond |
| 5,219,349 | A | 6/1993 | Krag et al. |
| 5,281,223 | A | 1/1994 | Ray |

(Continued)

FOREIGN PATENT DOCUMENTS

| | | |
|---|---|---|
| AU | 727020 | 11/2000 |
| CA | 2275952 | 10/2006 |

(Continued)

OTHER PUBLICATIONS

Examination Notice, dated Apr. 27, 2015, received in connection with corresponding EP Application No. 13193245.1.

(Continued)

*Primary Examiner* — Nicholas Plionis
(74) *Attorney, Agent, or Firm* — Meunier Carlin & Curfman LLC

(57) ABSTRACT

An anchor assembly for use in spinal fixation to interconnect a longitudinal spinal rod with a patient's vertebra. The anchor assembly preferably includes a bone anchor, a body with a rod-receiving channel, an insert member (preferably a bushing), and a locking cap. The anchor assembly enables in-situ assembly where the bone anchor may be secured to the patient's vertebra prior to being received within the body of the bone anchor assembly. Accordingly, the anchor assembly enables a surgeon to implant the bone anchor without the body to maximize visibility and access around the anchoring site. Once the bone anchor has been secured to the patient's vertebra, the body may be snapped onto the bone anchor and a spinal rod may be inserted into the rod-receiving channel.

14 Claims, 27 Drawing Sheets

(56) References Cited

U.S. PATENT DOCUMENTS

| | | |
|---|---|---|
| 5,385,565 A | 1/1995 | Ray |
| 5,478,340 A | 12/1995 | Kluger |
| 5,490,851 A | 2/1996 | Nenov et al. |
| 5,632,744 A | 5/1997 | Campbell, Jr. |
| 5,672,175 A | 9/1997 | Martin |
| 5,800,434 A | 9/1998 | Campbell, Jr. |
| 5,814,046 A | 9/1998 | Hopf |
| 6,090,113 A | 7/2000 | Le Couedic et al. |
| 6,551,316 B1 | 4/2003 | Rinner et al. |
| 6,726,692 B2 | 4/2004 | Bette |
| 6,746,449 B2 | 6/2004 | Jones et al. |
| 6,755,828 B2 | 6/2004 | Shevtsov et al. |
| 7,004,947 B2 | 2/2006 | Shluzas et al. |
| 7,188,626 B2 | 3/2007 | Foley et al. |
| 7,278,995 B2 | 10/2007 | Nichols et al. |
| 7,572,281 B2 | 8/2009 | Runco et al. |
| 7,611,517 B2 | 11/2009 | Lim |
| 7,618,444 B2 | 11/2009 | Shluzas |
| 7,625,376 B2 | 12/2009 | Brumfield et al. |
| 7,655,008 B2 | 2/2010 | Lenke et al. |
| 7,658,753 B2 | 2/2010 | Carl et al. |
| 7,670,358 B2 | 3/2010 | Barry |
| 7,686,814 B2 | 3/2010 | Lim et al. |
| 7,708,765 B2 | 5/2010 | Carl et al. |
| 7,722,617 B2 | 5/2010 | Young et al. |
| 7,744,598 B2 | 6/2010 | Brumfield et al. |
| 7,758,584 B2 | 7/2010 | Bankoski et al. |
| 7,776,072 B2 | 8/2010 | Barry |
| 7,776,074 B2 | 8/2010 | Bray |
| 7,794,464 B2 | 9/2010 | Bridwell et al. |
| 7,799,031 B2 | 9/2010 | Miller et al. |
| 7,811,288 B2 | 10/2010 | Jones et al. |
| 7,824,411 B2 | 11/2010 | Varieur et al. |
| 7,951,168 B2 | 5/2011 | Chao et al. |
| 7,951,175 B2 | 5/2011 | Chao et al. |
| 8,002,801 B2 | 8/2011 | Carl et al. |
| 8,007,516 B2 | 8/2011 | Chao et al. |
| 8,016,860 B2 | 9/2011 | Carl et al. |
| 8,043,333 B2 | 10/2011 | Frigg et al. |
| 2005/0245928 A1 | 11/2005 | Colleran et al. |
| 2006/0122597 A1 | 6/2006 | Jones et al. |
| 2006/0271050 A1 | 11/2006 | Piza Vallespir |
| 2007/0118123 A1* | 5/2007 | Strausbaugh ...... A61B 17/7032 606/272 |
| 2007/0288004 A1 | 12/2007 | Alvarez |
| 2008/0004629 A1 | 1/2008 | Nichols et al. |
| 2008/0154277 A1 | 6/2008 | Machalk et al. |
| 2008/0221626 A1 | 9/2008 | Butters et al. |
| 2008/0294206 A1 | 11/2008 | Choi et al. |
| 2009/0204159 A1 | 8/2009 | Justis et al. |
| 2009/0216237 A1 | 8/2009 | Frezal et al. |
| 2009/0228051 A1 | 9/2009 | Kolb et al. |
| 2009/0228054 A1 | 9/2009 | Hoffman et al. |
| 2009/0228055 A1 | 9/2009 | Jackson |
| 2009/0259262 A1 | 10/2009 | Nayet |
| 2009/0281582 A1 | 11/2009 | Villa et al. |
| 2010/0004695 A1 | 1/2010 | Stad et al. |
| 2010/0030283 A1 | 2/2010 | King et al. |
| 2010/0069972 A1 | 3/2010 | Jones et al. |
| 2010/0121385 A1 | 5/2010 | Blain et al. |
| 2010/0121386 A1 | 5/2010 | Peultier et al. |
| 2010/0152787 A1 | 6/2010 | Walsh et al. |
| 2010/0185242 A1 | 7/2010 | Barry et al. |
| 2010/0185248 A1 | 7/2010 | Barry et al. |
| 2010/0228302 A1 | 9/2010 | Dauster et al. |
| 2010/0234902 A1 | 9/2010 | Biedermann et al. |
| 2010/0280560 A1 | 11/2010 | Brumfield et al. |
| 2010/0318129 A1 | 12/2010 | Seme et al. |
| 2012/0010661 A1 | 1/2012 | Farris et al. |
| 2012/0035670 A1 | 2/2012 | Jackson et al. |
| 2012/0136395 A1 | 5/2012 | Biedermann et al. |
| 2012/0209336 A1 | 8/2012 | Jackson et al. |

FOREIGN PATENT DOCUMENTS

| | | |
|---|---|---|
| DE | 69723107 | 2/2004 |
| EP | 528177 | 9/1996 |
| EP | 553782 | 4/1997 |
| EP | 955930 | 6/2003 |
| EP | 1374786 | 2/2004 |
| EP | 1392190 | 8/2006 |
| JP | 10-248855 A | 9/1998 |
| JP | 2000-350731 | 12/2000 |
| WO | 2012/091737 | 7/2012 |

OTHER PUBLICATIONS

Extended European Search Report, mailed Feb. 17, 2014, received in connection with European Application No. 13193245.1.

* cited by examiner

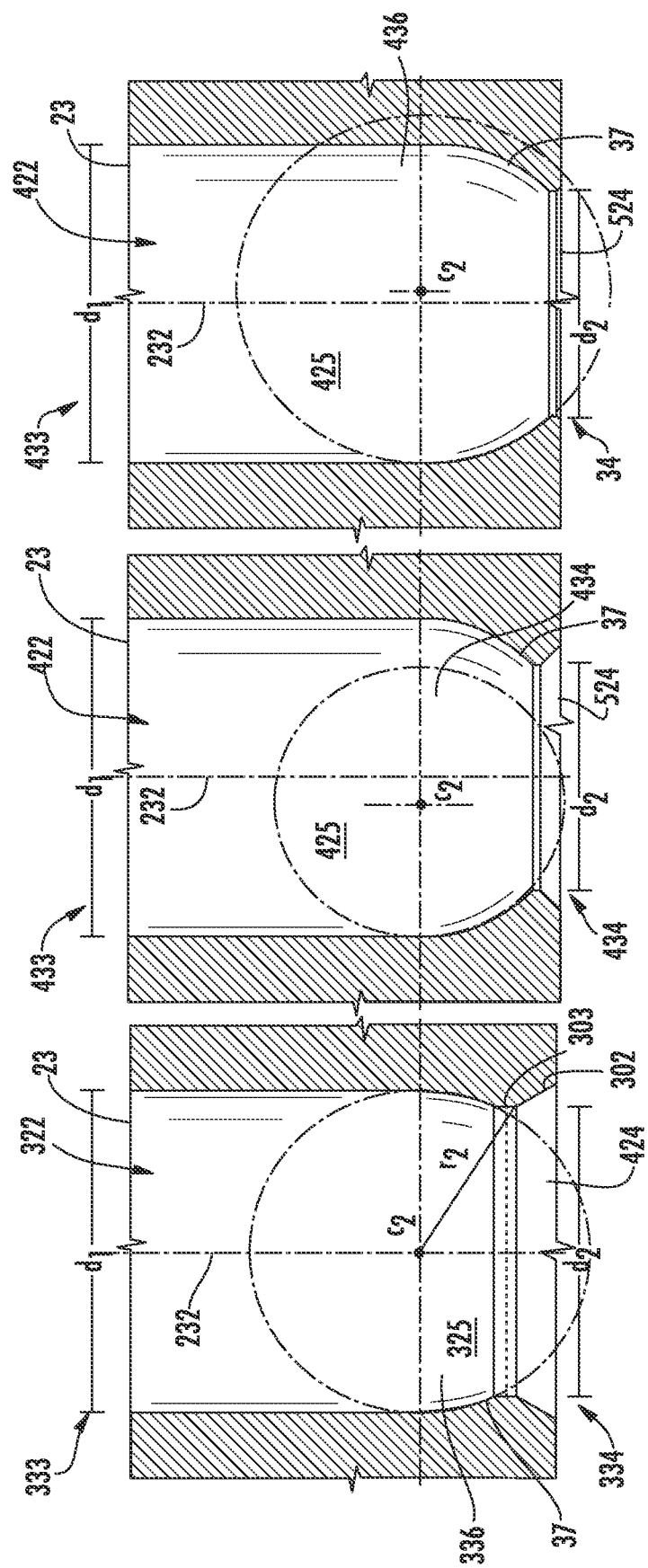

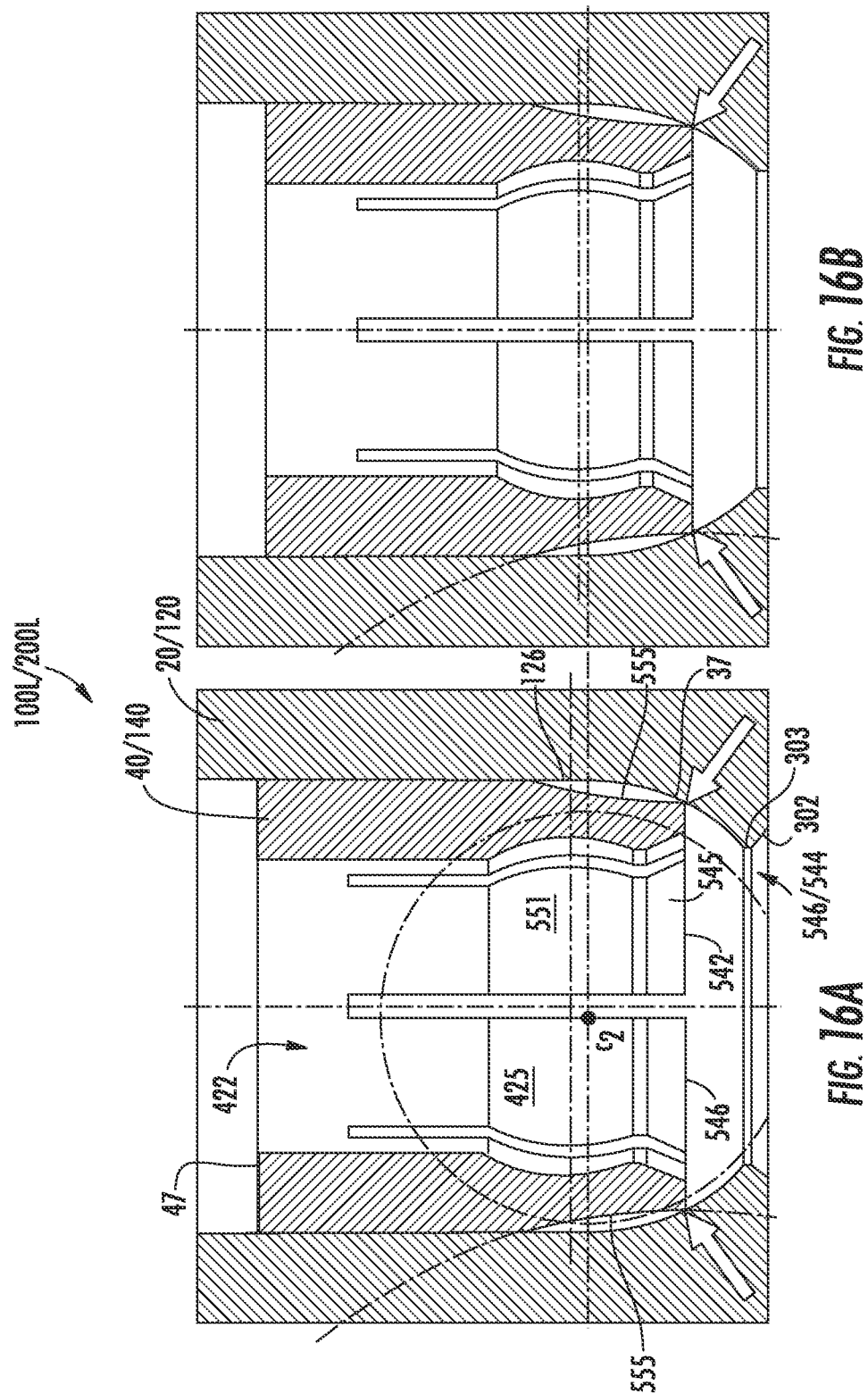

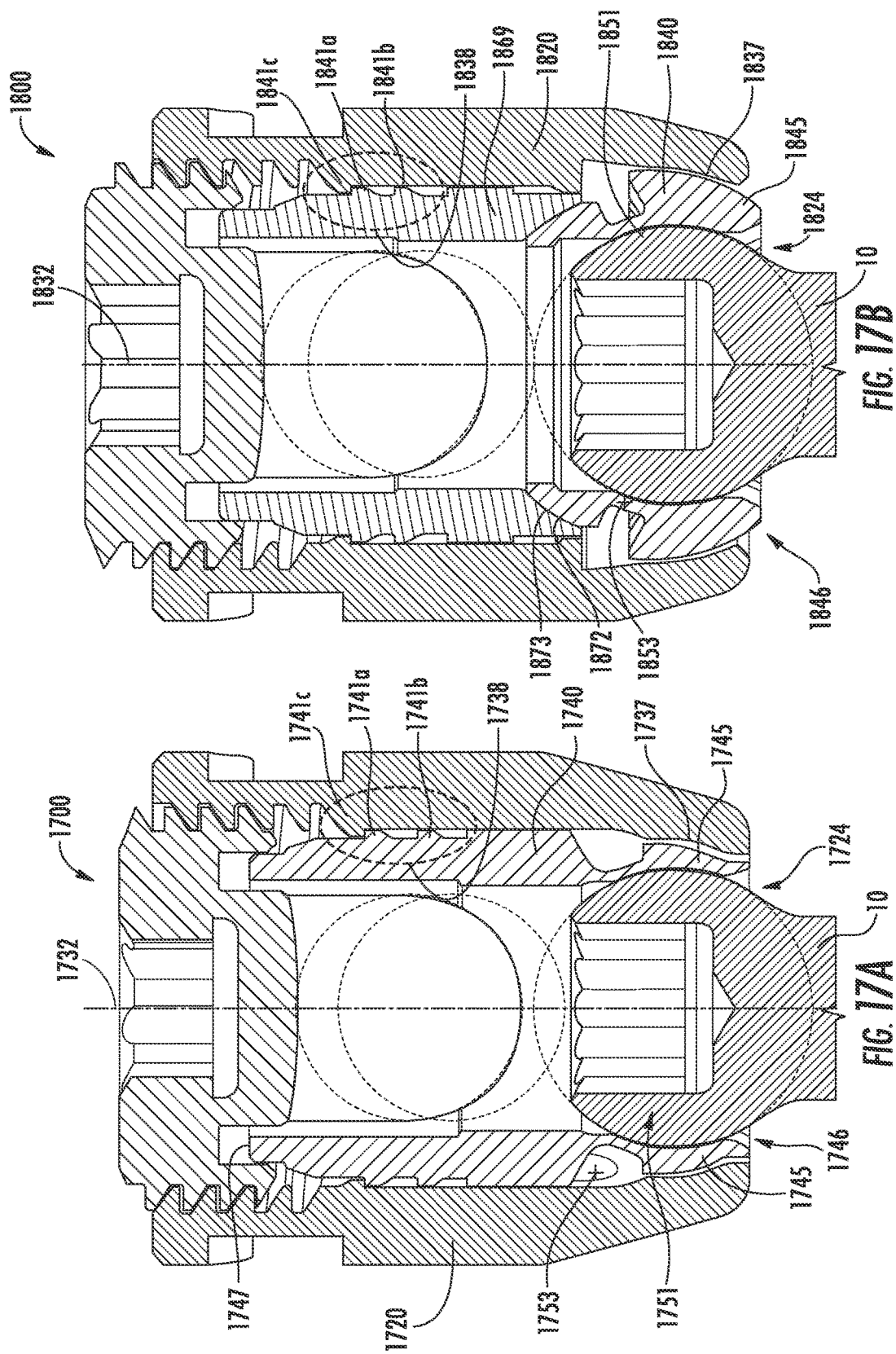

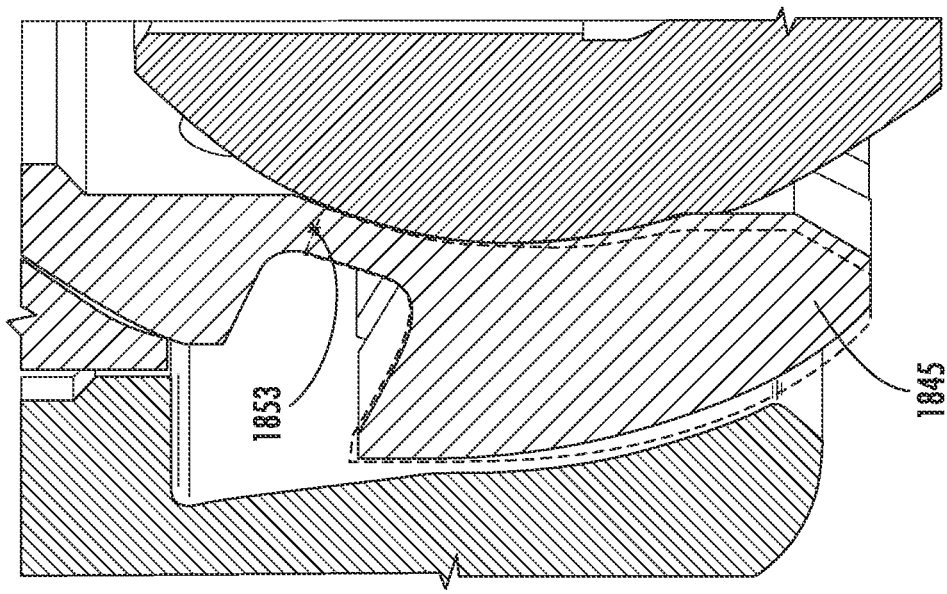
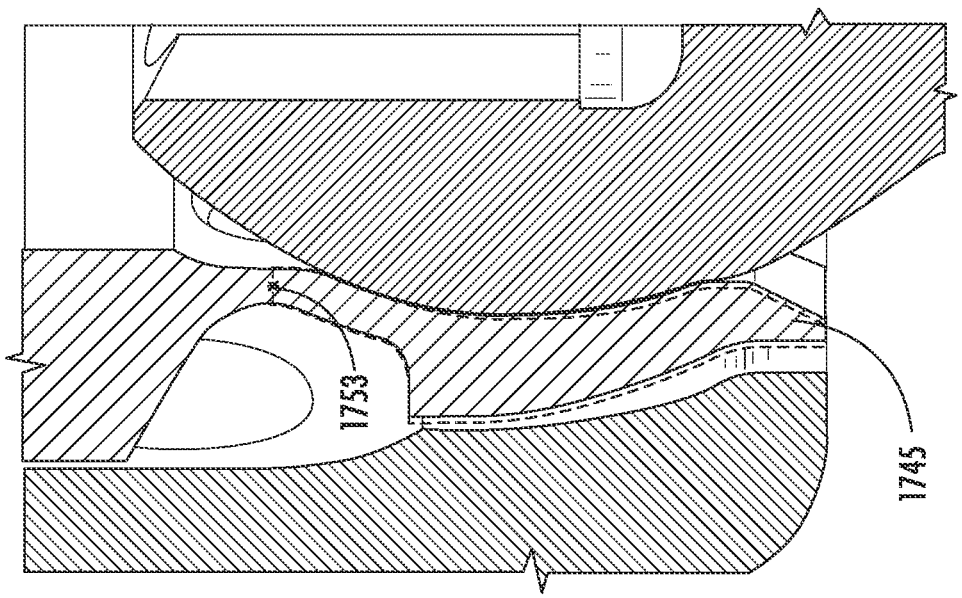

BONE FIXATION ASSEMBLY

CROSS-REFERENCE TO RELATED APPLICATIONS

This application claims the benefit of U.S. Patent Application No. 61/727,290, filed Nov. 16, 2012, titled "Bone Fixation Assembly," and U.S. Patent Application No. 61/731,772, filed Nov. 30, 2012, titled "Reduction Tool for Use with Bone Fixation Assembly," the contents of which are hereby incorporated by reference.

BACKGROUND

As a result of various spinal disorders, it often is necessary to surgically correct and stabilize spinal curvatures, or to facilitate spinal fusion. Numerous systems for treating spinal disorders have been developed. For example, one example includes a bone fixation system that has a pair of elongated members, typically spinal rods, longitudinally placed on the posterior spine on either or both sides of the spinous processes of the vertebral column. Each rod is attached to various vertebrae along the length of the spine by way of bone fixation or bone anchor assemblies, e.g., pedicle screws. The body of the pedicle screw often has a rod-receiving channel and receives a locking cap to secure the spinal rod to the pedicle screw. To facilitate insertion of the spinal rod into the rod-receiving channels of the pedicle screws, pedicle screws have been developed wherein the body is separate from and pivotable with respect to the bone anchor (commonly known as polyaxial pedicle screws).

SUMMARY

The present disclosure relates generally to orthopedics. In more particularity, the present disclosure is directed to a bone anchor assembly for use in a spinal fixation procedure that connects a support member (e.g., a spinal rod) to a vertebra. The anchor assembly preferably includes a bone anchor having a head portion (e.g., a bone screw), an insert member (e.g., a bushing), a body having a bore for receiving the insert member and a rod receiving channel, and a locking cap engageable with the body and for receiving the spinal rod. The bone anchor assembly preferably enables in-situ assembly. That is, the anchor assembly may be configured so that in use, the bone anchor may be secured to the patient's vertebra prior to being connected to the body. Accordingly, the anchor assembly preferably enables a surgeon to implant the bone anchor without the body and bushing to maximize visibility and access around the anchoring site. Once the bone anchor has been secured to the patient's vertebra, the body can "click-on" to the bone anchor.

In some implementations, the anchor assembly includes bone anchor moveable with respect to a body subassembly prior to fixing the position of the spinal support member to the body subassembly. The body subassembly may be sized and configured to snap onto the head of the bone anchor and may include an insert member (e.g., a bushing), and receives a locking cap. The head portion preferably may include a first tool interface for engaging a first surgical instrument operatively associated with the bone anchor. The body preferably includes a longitudinal axis, an interior wall, an upper end with an upper opening, a lower end with a lower opening, a bore extending between the upper opening and the lower opening, and a rod-receiving channel. The rod-receiving channel may be configured and arranged to receive a spinal rod.

The bushing may include an upper end and a lower portion that captures, and at least partially surrounds, the head portion of the bone anchor. The lower portion of the bushing includes at least one, preferably a plurality of, slot(s) extending from the lower end, the slots preferably defining a plurality of flexible arms, wherein each of the flexible arms have an outer surface. The bushing may be movably positionable within the bore of the body.

Other systems, methods, features and/or advantages will be or may become apparent to one with skill in the art upon examination of the following drawings and detailed description. It is intended that all such additional systems, methods, features and/or advantages be included within this description and be protected by the accompanying claims.

BRIEF DESCRIPTION OF THE DRAWINGS

The foregoing summary, as well as the following detailed description of preferred embodiments of the disclosure, will be better understood when read in conjunction with the appended drawings. The preferred embodiments of a bone anchor system including a bone anchor assembly are shown in the drawings for the purposes of illustration. It should be understood, however, that the application is not limited to the precise arrangements, structures, features, embodiments, instrumentalities, and methods shown and described, and the arrangements, structures, features, embodiments, instrumentalities, and methods shown and described may be used singularly or in combination with other arrangements, structures, features, embodiments, instrumentalities, and methods. In the drawings:

FIGS. 3A-3E illustrate various configurations of a body of the bone anchor assembly;

FIGS. 16A-16B illustrate a front sectional view of an eleventh embodiment of a polyaxial pedicle screw assembly of the present disclosure;

FIGS. 17A and 18A illustrate a third embodiment of bone anchor or bone fixation assembly; and FIGS. 17B and 18B is illustrated a fourth embodiment of bone anchor or bone fixation assembly.

DETAILED DESCRIPTION

Figure 1A:
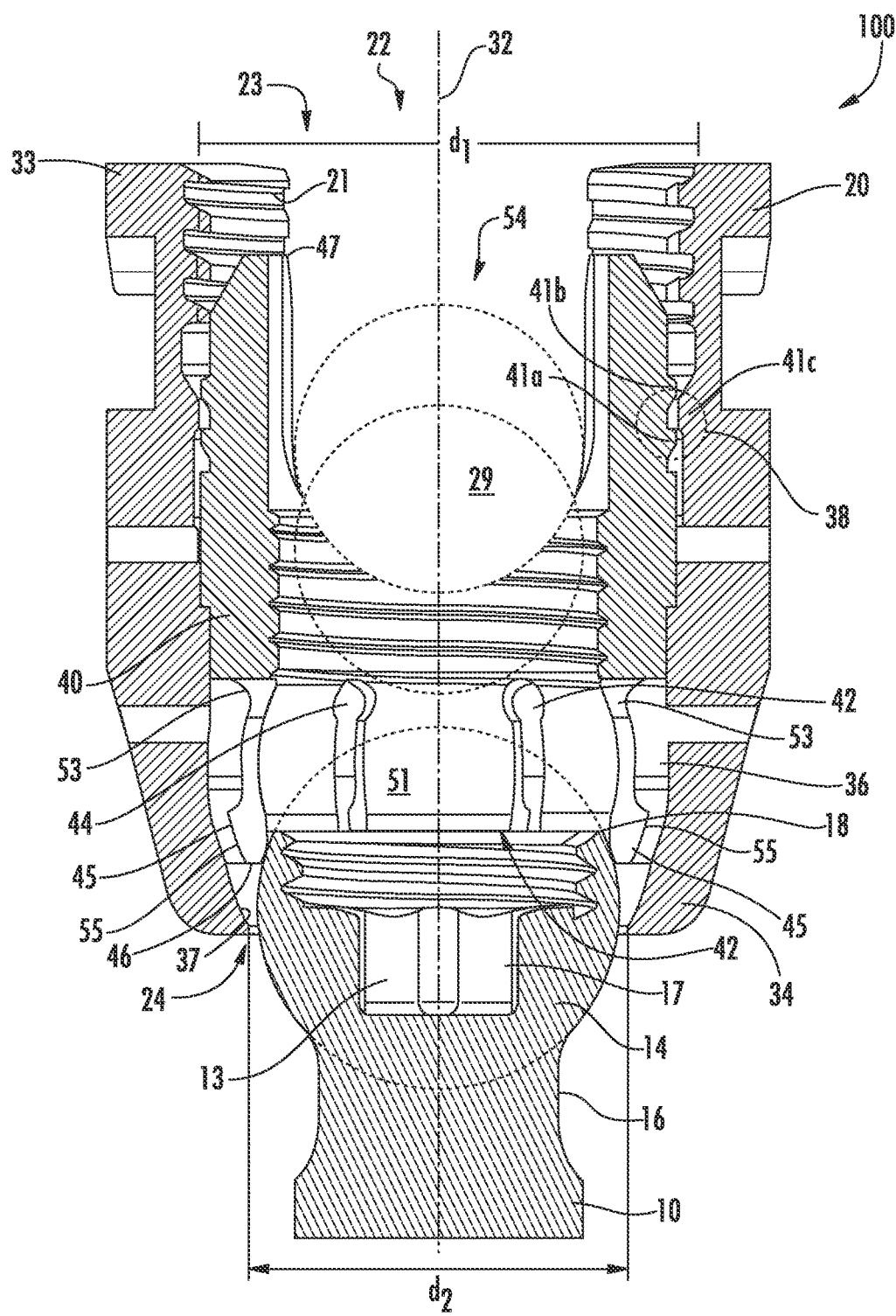
FIGS. 1A-1D illustrate a side perspective view of a first embodiment of a bone anchor assembly in accordance with the present disclosure.
Figure 1B:
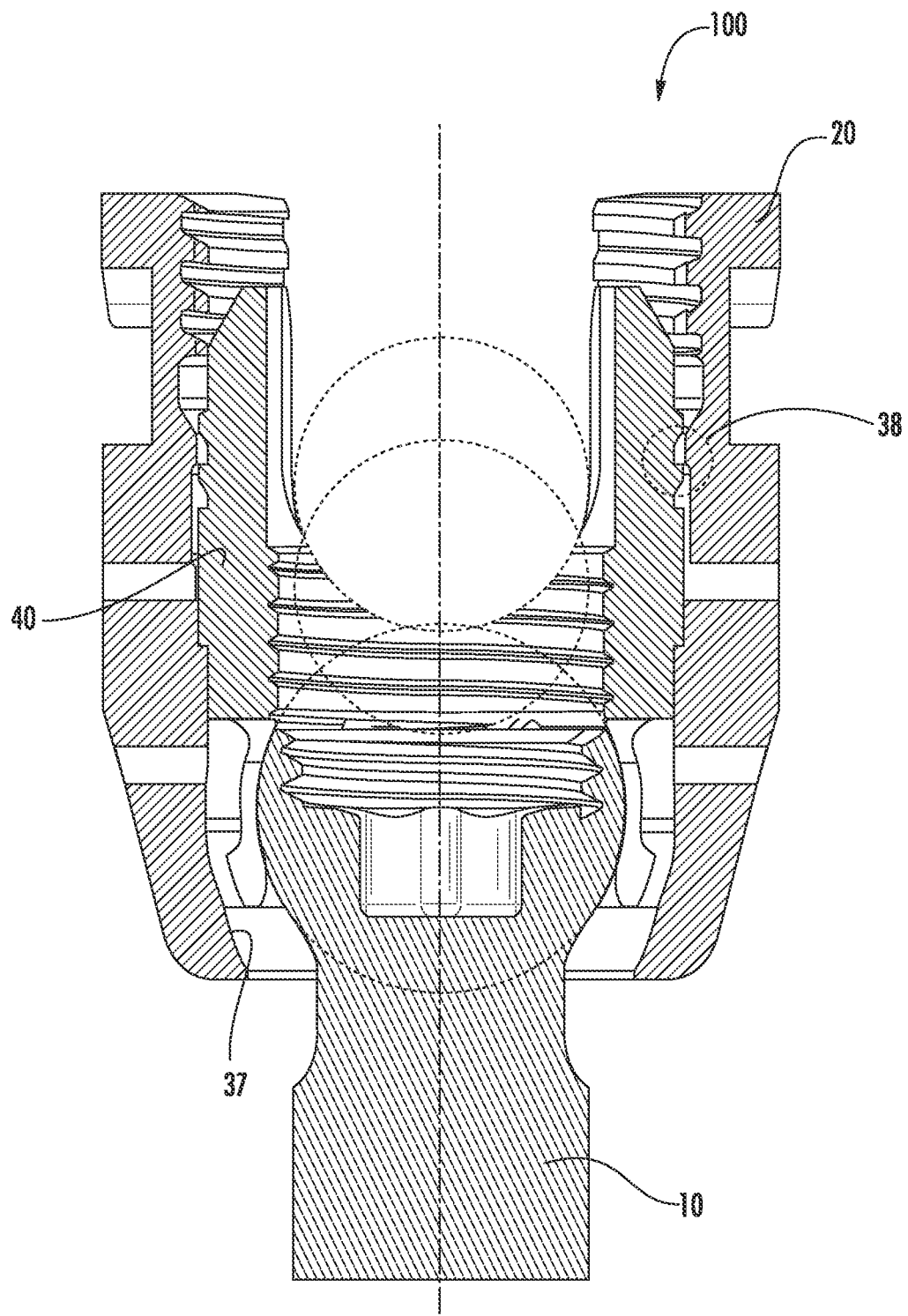

Certain terminology is used in the following description for convenience only and is not limiting. The words "right", "left", "lower", "upper", "below", "above", "top", and "bottom" designate directions in the drawings to which reference is made. The words "inwardly" or "distally" and "outwardly" or "proximally" refer to directions toward and away from, respectively, the geometric center of the bone anchor system and/or assembly, the described instruments and designated parts thereof. The words, "anterior", "posterior", "superior", "inferior", "medial", and "lateral" and related words and/or phrases designate preferred positions and orientations in the human body to which reference is made and are not meant to be limiting. The terminology includes the above-listed words, derivatives thereof and words of similar import.

Certain exemplary implementations of the disclosure will now be described with reference to the drawings. In general, such implementations relate to a polyaxial bone fixation element by way of non-limiting example and a polyaxial bone fixation element for use in spinal fixation to facilitate insertion of a longitudinal spinal rod in a rod-receiving channel formed in the body of the polyaxial bone fixation element. The implementations may have other applications and uses and should not be limited to the structure or use described and illustrated.

Referring to FIGS. 1A-1D, there is illustrated an implementation of bone anchor or bone fixation assembly 100 that generally includes a bone anchor 10 (e.g., a bone screw), a body 20, a bushing 40, and a locking cap 92. By way of introduction, and as will be described in greater detail below, the anchor assembly 100 enables in-situ assembly of the bone anchor 10 to the body 20 of the anchor assembly 100 such that the bone anchor 10 may be secured to a patients vertebra prior to being received within the body 20. Thus, the bone fixation assembly 100 enables a surgeon to implant the bone anchor 10 without the body 20 and bushing 40 being pre-assembled to the bone anchor 10. By enabling the surgeon to implant only the bone anchor 10 without the body 20, the anchor assembly 100 of the present disclosure maximizes surgeon visibility and access around the anchoring site.

Once the bone anchor 10 has been secured to the patients vertebra, the body 20 and bushing 40 (retained in the body 20), may be "clicked-on" to the bone anchor 10. Accordingly, in the anchor assembly 100, the bone anchor 10 enters the body 20 through a lower opening 24 of the body 20. Once the body 20 and bushing 40 have been clicked-on to the bone anchor 10, a spinal rod may be inserted into a rod receiving channel 29, and the locking cap 92 maybe used to secure the position of the rod and the bushing 40 within the body 20. Alternatively, the bone fixation assembly 100 (e.g., the body 20, bushing 40, and bone anchor 10) may be provided pre-assembled using components identical to or substantially similar to the components described herein.

The bone fixation assembly 100 may be generally used in the spine (for example, in the lumbar, thoracic or cervical regions), and in particular attached to the vertebra. Those skilled in the art will appreciate that the anchor assembly 100 may be used for fixation of other parts of the body such as, for example, joints, long bones, ribs, or bones in the hand, face, feet, toe, extremities, cranium, mandible, etc., and may be used for non-orthopedic applications and non-medical applications.

With the above introduction, the bone fixation assembly 100 will be described. Constituent components of the bone fixation assembly 100 will now be described—the bone anchor 10, the body 20, the bushing 40 and the locking cap 92. In accordance with some implementations, the bone anchor 10 is in the form of a bone screw. Alternatively, the bone anchor 10 may be, for example, a hook, pin, blade, nail, tack, stake or other fastener such as, a clamp, an implant, etc. The bone anchor 10 may include an enlarged head 14 and an externally threaded shaft portion (not shown) for engaging a patient's vertebra. The features of the shaft including, for example, thread pitch, shaft diameter, shaft shape, etc. may be varied, as it would be apparent to one of ordinary skill in the art. The bone anchor 10 is not limited to any particular features on or type of shaft. The bone anchor 10 may also include a reduced diameter neck portion 16 between the head 14 and the shaft portion, which facilitates the polyaxial nature of the bone fixation assembly 100, shown in FIG. 1D. Although not shown, the bone anchor 10 may be cannulated and fenestrated such that openings extend outwardly from a central hollow channel in the cannulated screw for a multitude of potential uses, including, but not limited to, urging material out of the screw during injection, drawing fluid into the central hollow channel from the sides of the screw to extract material adjacent the screw, or passing through instruments or implants.

The head 14 may include a drive surface 17 for receiving a corresponding tip of a drive tool, such as a screwdriver, to rotate the bone anchor 10 into engagement with the patient's vertebra. The drive surface 17 may have any form including, but not limited to, an external hexagon, a star drive pattern, a Phillips head pattern, a slot for a screw driver, a threading for a correspondingly threaded post, etc. As shown, the drive surface 17 may include a first tool interface 13 that may include an external drive feature that engages a female-type driver. The specific shape of the drive surface 17 or first tool interface 13 may be chosen to cooperate with the corresponding drive tool. The head 14 may also include a second tool interface 18 or a sleeve interface. The second tool interface 18 may include threading (as shown) or other features to interact with instruments, such as a drive instrument. The head 14 may have a curved or semi-spherical shape to facilitate rotation and angulation with respect to the bushing 40 before or after the bone anchor 10 is locked to the body 20, as will be described in greater detail below.

The body 20 may generally be described as a cylindrical tubular body having a rod receiving channel 29, a longitudinal axis 32, an upper end 33 having an upper opening 23, a lower end 34 having a lower opening 24, and an axial bore 22 substantially coaxial with the longitudinal axis 32 of the body 20. The axial bore 22 extends from the upper opening 23 to the lower opening 24 and has a lower chamber 36 proximate the lower end 34. The axial bore 22 at the upper opening 23 has a first diameter d1 and the bore 22 at the lower opening 24 has a second diameter d2, which may be smaller than the first diameter d1. The second diameter d2 may be sized and configured so that the head 14 of the bone anchor 10 may be passed through the lower opening 24 of the body 20. An inner surface of the axial bore 22 includes a plurality of threads 21 in the upper end 33 for engaging the locking cap 92. In accordance with aspects of the disclosure, the body 20 and axial bore 22 may have any mounting structure for engaging the locking cap 92 including, but not limited to, external threads, cam-lock, quarter lock, clamps, lugs, bayonets, etc.

The bushing 40 includes an upper end 47 having an upper opening 54, a lower end portion 46 having a lower opening 42, and a bore that extends from the upper opening 54 to the lower opening 42. A drive tool, such as, for example, a screw driver, can be inserted through the bore of the bushing 40 and into engagement with the bone anchor 10 so that the bone anchor 10 may be rotated into engagement with the patient's vertebra. The bushing 40 also includes an exterior surface 55, which may be sized and configured to contact lower chamber surfaces 37 of the body 20 when the head 14 of the bone anchor 10 is secured within the bushing 40 in a locked position, as will be detailed further below with reference to FIGS. 1C-1D. The lower end portion 46 of the bushing 40 includes an interior cavity 51 that has a predetermined size to receive and secure the head 14 of the bone anchor 10 so that the bone anchor 10 can rotate polyaxially through a range of angles with respect to the bushing 40 and hence with respect to the body 20, as shown in FIG. 1D.

Figure 1C:
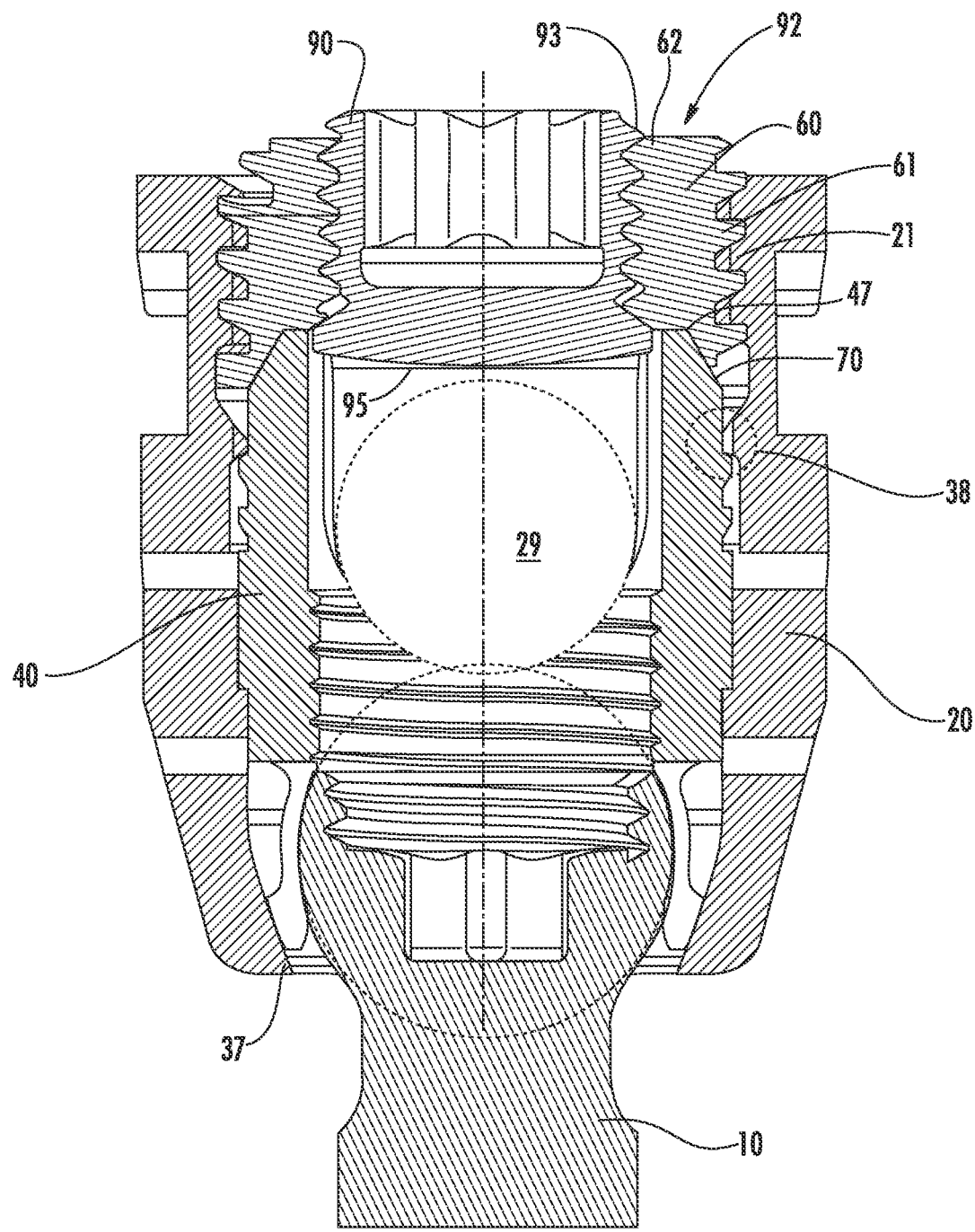
Figure 1D:
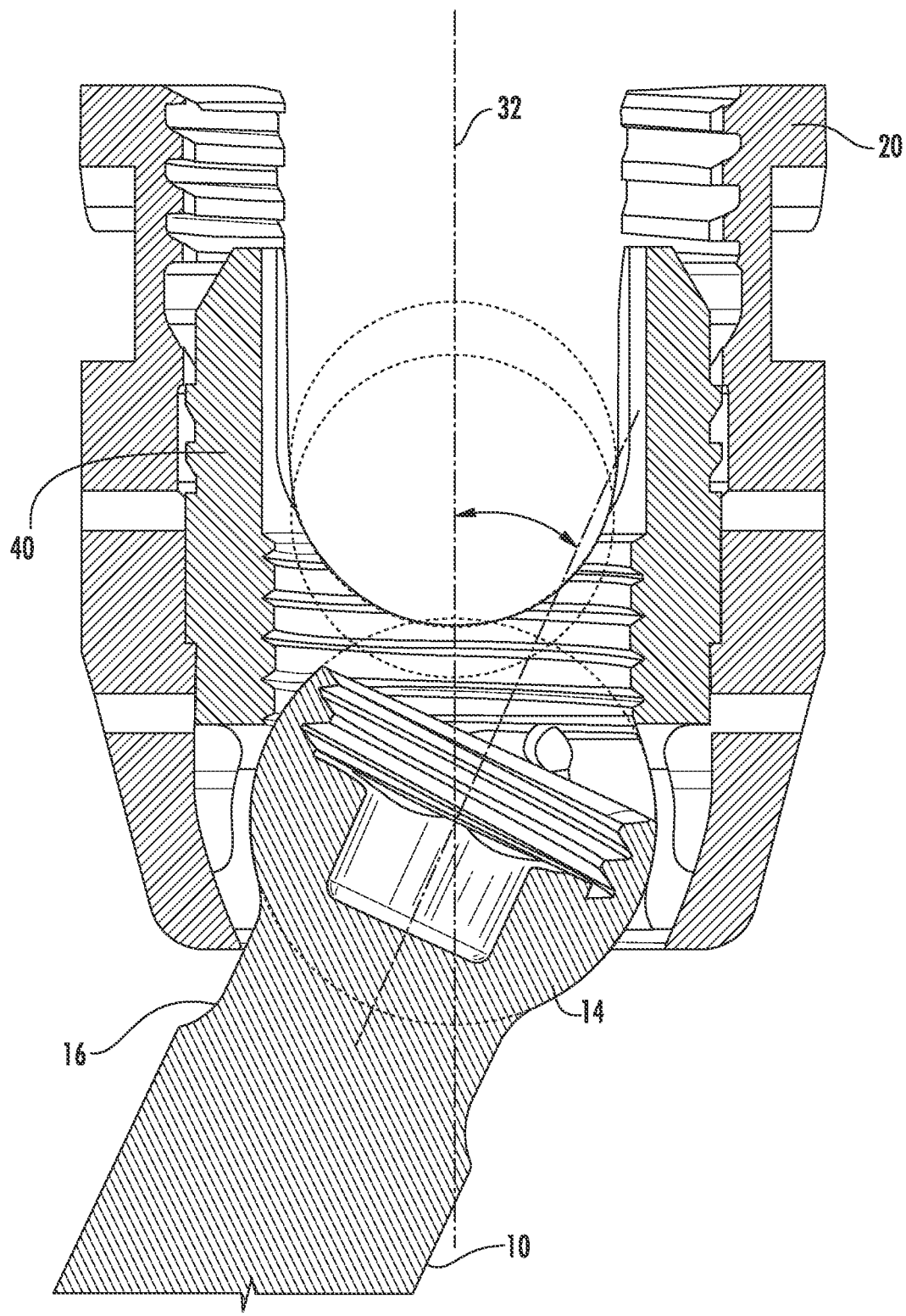

The bushing 40 is may be placed into the lower chamber 36 of the body 20 during manufacture and is permitted to move within a portion of the axial bore 22 formed in the body 20 between a first (loading/unlocked) position (see, FIGS. 1A-1B) and a second (loaded/locked) position (see, FIGS. 1C-1D). That is, the bushing 40 is moveable within the body 20 between the first position where the bone anchor 10 can be connected to or unconnected from the bushing 40, and the second position where the bone anchor 10 is locked with respect to the bushing 40. The bushing 40 is sized and configured such that it may be inserted into the body 20 through the upper opening 23, but is prevented from exiting through the lower opening 24.

To place and retain the bushing 40 in the body 20, the bushing 40 may be provided with structures, features, geometry and a configuration that interacts and interfaces with structures, features and geometry of the body 20. In an example, the bushing 40 and body 20 may be provided with one or more ratchet teeth 41 as part of a locking mechanism 38 to prevent the bushing 40 from moving out of the body 20 through upper opening 23 and to lock the bushing 40 into a predetermined orientation within the body 20 when in the first (loading/unlocked) position (FIGS. 1A-1B) and the second (loaded/locked) position (FIGS. 1C-1D). Thus, once the bushing 40 is placed and assembled into the body 20, the bushing 40 is retainable within the body 20 such that the bushing 40 is generally prevented from (1) passing back up through the upper opening 23 formed in the body 20; and (2) passing through the lower opening 24 formed in the body 20.

As with be described with reference to FIGS. 4A-4D, the interior cavity 51 formed in the bushing 40 may have a curvate or semi-spherical shape for receiving the curvate or semi-spherical head 14 of the bone anchor 10. The interior cavity 51 formed in the bushing 40 may be constructed so that the bone anchor 10 can polyaxially rotate with respect to the bushing 40, and hence, with respect to the body 20.

The bushing 40 also includes one or more slots 44 extending from the lower end portion 46 thereof so that at least a portion of the bushing 40 is radially expandable so that the head 14 of the bone anchor 10 can be inserted through the lower opening 42 in the lower end portion 46 and into the interior cavity 51 of the bushing 40 and/or radially compressible to compress or lock against the head 14 of the bone anchor 10 when radial forces are applied thereto. The slots 44 may extend from the lower end 46, the upper end 47 or both ends 46, 47. One slot 42 may extend the length of the bushing 40 creating a compressible spring clip.

To interconnect or attach the bone anchor 10 to the body 20, the body 20 may be provided with the bushing 40 pre-assembled therein and in the loading position, as shown in FIG. 1A. In this position, a lower tooth 41a of an upper portion of the bushing 40 engages a tooth 41c of the body in the locking mechanism 38. The head 14 of the bone anchor 10 may then be inserted into the lower opening 24 of the body 20 and into the interior cavity 51 of the bushing 40.

Next, as shown in FIG. 1C, after the head 14 of the bone anchor 10 is fully inserted into the cavity 51 of the bushing 40, the bushing 40 is moved down into the lower chamber 36 of the body 20 to prevent the head 14 of the bone anchor 10 from becoming dislodged from bushing 40. The downward movement causes the upper portion of the bushing 40 to be retained within the body 20 by the interaction of the tooth 41b engaging the tooth 41c of the body 20. The downward movement also moves the bushing 40 toward the lower opening 24 of the body 20 to lock the head 14 of the bone anchor 10. In particular, as the bushing 40 moves downwards, the arms 45 of the bushing 40 come into contact with the one or more lower chamber surfaces 37 in the lower chamber 36 of the body 20, which exert a force against the arms 45 of the bushing 40, causing the arms 45 to collapse around the head 14 of the bone anchor 10 and into the locking position, thereby locking the position of the bone anchor 10 relative to the body 20. More particularly, as the bushing 40 moves downward, the bushing arms 45 preferably contact the outer spherical surface of the head 14 and the bushing arms 45 are urged radially inward about the head 14 of the bone anchor 10 by the lower chamber surfaces 37. Thus, the head 14 is "clicked-in" to the bushing 40 and the flexible arms 45 retain the head 14 within the cavity 51.

Referring to FIG. 1D, when the bone anchor 10 is in the locked position the head 14 is able to rotate polyaxially within the cavity 51, and thus about the body 20. As illustrated, the neck portion 16 acts as a stop when the neck portion 16 contacts the lower and 34 of the bushing 40. Accordingly, the bushing 40 of the first implementation, provides for approximately 25° of angulation in any direction with respect to the longitudinal axis 32.

Referring again to FIG. 1C, the locking cap 92 is movable from an unlocked to a locked position to lock the bone anchor 10 and the rod (not shown) in place within the body 20. In some implementations, the locking cap 92 permits separate locking of the bushing 40 and bone anchor 10, and the rod. For example, in a configuration, the locking cap 92 may include a setscrew 90 that is received within a threaded ring 60. The threaded ring 60 includes exterior threads 61 and interior threads 62. The exterior threads 61 of the threaded ring 60 are threadably engageable with the interior threads 21 of the body 20. The setscrew 90 includes external threads 93 capable of threadably engaging the interior threads 62 of the threaded ring 60. The threaded ring 60 and setscrew 90 may be preassembled as a unit for use during the implantation of the anchor assembly 100. Alternatively, the threaded ring 60 and set screw 90 may be supplied and assembled during the surgical implantation of the bone fixation assembly 100.

With reference to FIG. 1C, to lock the bone anchor 10 once the rod is placed into the rod receiving channel 29, the locking cap 92 may be placed into the upper opening 23 of the body 20. The threaded ring 60 may then be threadably engaged with the threads 21 of the body 20 to connect the locking cap 92 to the body 20. By engaging the locking cap 92 with the body 20, the rod-receiving channel 29 is closed and the spinal rod is captured and retained in the bone fixation assembly 100. To lock the movement of the spinal rod and the bone anchor 10 with respect to the body 20, the threaded ring 60 is tightened and moves downward in the body 20. As the threaded ring 60 is moved further downward in the body 20, the threaded ring 60 pushes down on the upper end 47 and angled section 70 which pushes down on bushing 40, causing the arms 45 of the bushing 40 to further collapse around the head 14 of the bone anchor 10, thereby securing the bushing 40 in the locked position, thus securing the position of the bone anchor 10 with respect to the body 20. As such, the threaded ring 60 controls the locking of the bone anchor 10.

In accordance with the above, to lock the rod in place, the setscrew 90 is tightened and as the setscrew 90 moves down within the bore of the threaded ring 60, the bottom surface 95 of the setscrew 90 pushes down on the rod, thereby securing the position of the rod. This configuration provides the benefit of the anchor assembly 100 having a low profile when assembled.

The bone fixation assembly 100 may be provided to a user in a kit including (1) bone anchors, (2) locking caps, (3) pre-assembled bushing body subassemblies, bushing/sleeve/body subassemblies, or fastener element body subassemblies, and (4) spinal rods. The pre-assembled bushing body subassemblies, bushing/sleeve/body subassemblies or fastener element/body subassemblies may be assembled during manufacture by inserting the bushing 40 into the axial bore 22 formed in the body 20 through the upper opening 23 formed in the body 20 until the bushing 40 is captured and retained in the body. The kit may be delivered to the user for use in, e.g., spinal surgery. During surgery, the surgeon may identify a level of the spine where the surgery will take place, makes an incision to expose the selected area and implants one or more bone anchors into the desired vertebrae. The subassembly may be clicked-on to the bone anchor 10 by urging the head 14 through the lower opening 24 in the body 20. Accordingly, the body subassembly may be engaged with the head 14 of the bone anchor 10 in situ. The anchor assembly including the bone anchor 10, the bushing 40, the body 20, and the locking cap 92 may be made from any biocompatible material including, but not limited to, metals such as, for example, titanium, titanium alloys, stainless steel, cobalt chromium, Nitinol, etc. Other materials such as, for example, composites, polymers, ceramics, and any other material may be used for the anchor assembly, its component parts, and spinal rods.

Referring to FIGS. 2A-2D, there is illustrated a second implementation of a bone anchor or bone fixation assembly 200 that generally includes a bone anchor 10 (e.g., a bone screw), a body 120, a bushing 140, and a locking cap 92. The elements of the second implementation that are the same as the first implementation of FIGS. 1A-1D will not be described again below. The body 120 may generally be described as a cylindrical tubular body having a rod receiving channel 129, a longitudinal axis 132, an upper end 133 having an upper opening 123, a lower end 134 having a lower opening 124, and an axial bore 122 substantially coaxial with the longitudinal axis 132 of the body 120. The axial bore 122 extends from the upper opening 123 to the lower opening 124 and has a lower chamber 136 having ledges 149.

The axial bore 122 at the upper opening 123 has a first diameter d11 and, at the lower opening 24, has a second diameter d12, which may be smaller than the first diameter d11. The second diameter d12 may be sized and configured so that the head 14 of the bone anchor 10 may be passed through the lower opening 124 of the body 120. An inner surface of the axial bore 122 includes a plurality of threads 121 in the upper end for engaging the locking cap 92. The body 120 and the axial bore 122 may have nearly any mounting structure for engaging the locking cap 192 including, but not limited to, external threads, cam-lock, quarter lock, clamps, lugs, bayonets, etc.

Figure 2A:
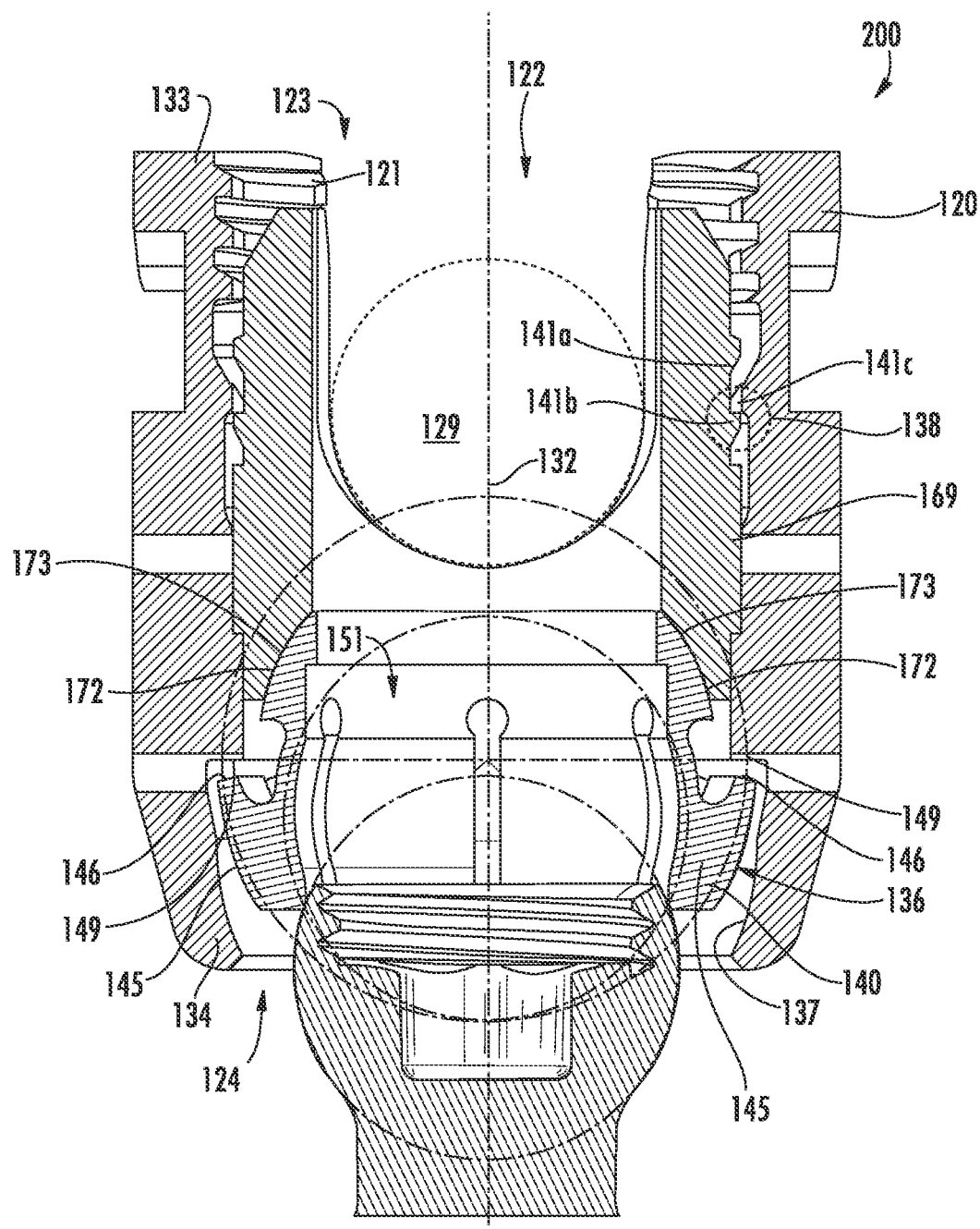
FIGS. 2A-2F illustrate a side perspective view of a second embodiment of a bone anchor assembly in accordance with the present disclosure.
Figure 2B:
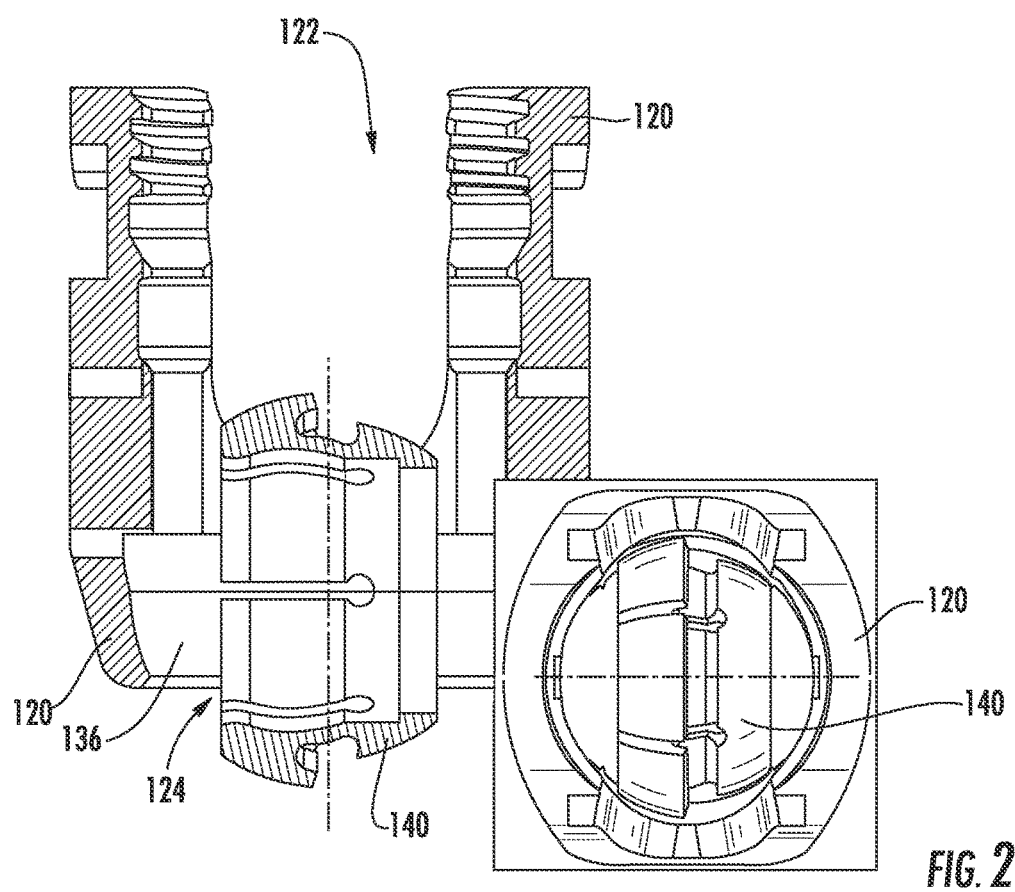
Figure 2C:
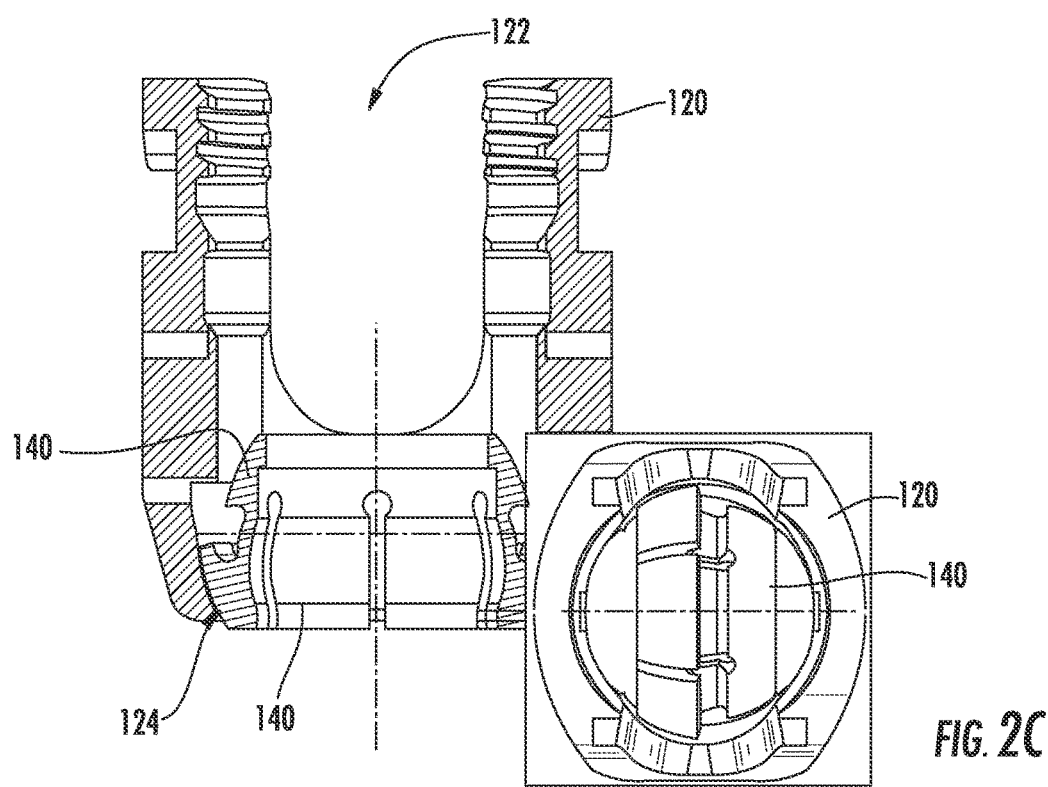

As shown in FIG. 2B-2C, the bushing 140 is sized and configured such that it may be inserted into the body 120 through the upper opening 123, but is prevented from exiting through the lower opening 124. As shown in FIG. 2B, the bushing 140 may be inserted into the body 120 in a rotated state, e.g., such that a longitudinal axis of the bushing 140 is perpendicular to the longitudinal axis 132 of the body 120. Once a portion of the bushing 140 passes through the lower opening 124, the bushing may be rotated such that the longitudinal axis of the bushing 140 is co-axial with the longitudinal axis 132 of the body 120 and such that the bushing 140 is positioned within the lower chamber 136 of the body 120 (FIG. 2C).

To place and retain the bushing 140 in the body 20, the saddle 169 preferably may be provided with structures, features, geometry and a configuration that interacts and interfaces with structures, features and geometry of the body 120 and the bushing 140. In an example, the saddle 169 and body 20 may be provided with one or more ratchet teeth 141 as part of a locking mechanism 138 to prevent the bushing 140 from moving out of the body 120 through upper opening 123 and to lock the bushing 140 into a predetermined orientation within the body 120 when in the first (loading/unlocked) position (FIGS. 2A and 2D) and the second (loaded/locked) position (FIGS. 2E-2F).

Referring again to FIG. 2A, once the bushing 140 is placed and assembled into the body 120, the bushing 140 may be retained within the body 120 by a saddle 169 such that the bushing 140 is generally prevented from (1) passing back up through the upper opening 123 formed in the body 120; and (2) passing through the lower opening 124 formed in the body 120. For example, after the bushing 140 is rotated and positioned as shown in FIG. 2C, the saddle 169 may be inserted into the upper opening 123 such that a lower surface 173 of the saddle 169 contacts an upper surface 172 of the bushing 140. As such, the bushing 140 is retained within the lower chamber 136 of the body 120.

Figure 2D:
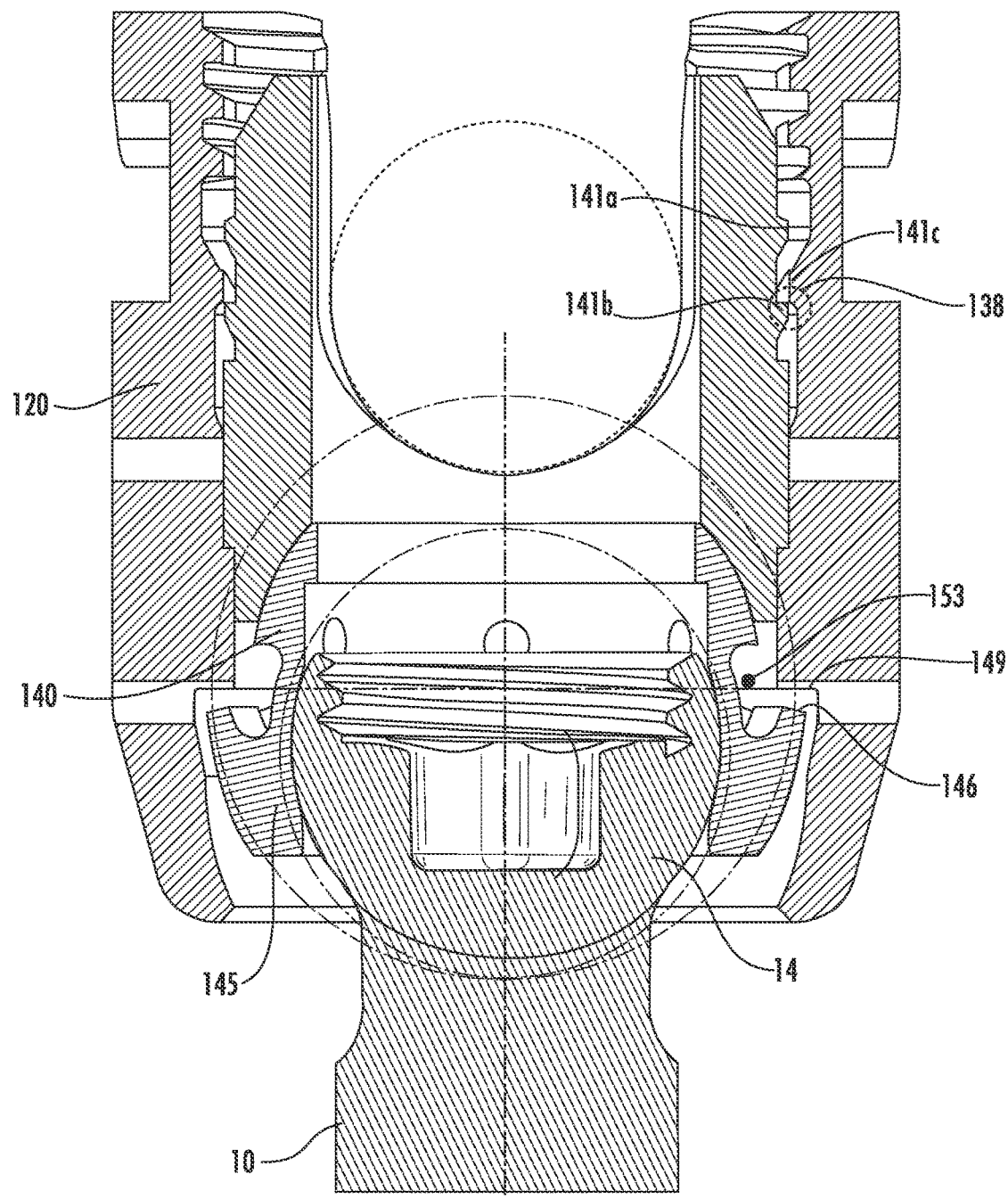
Figure 2E:
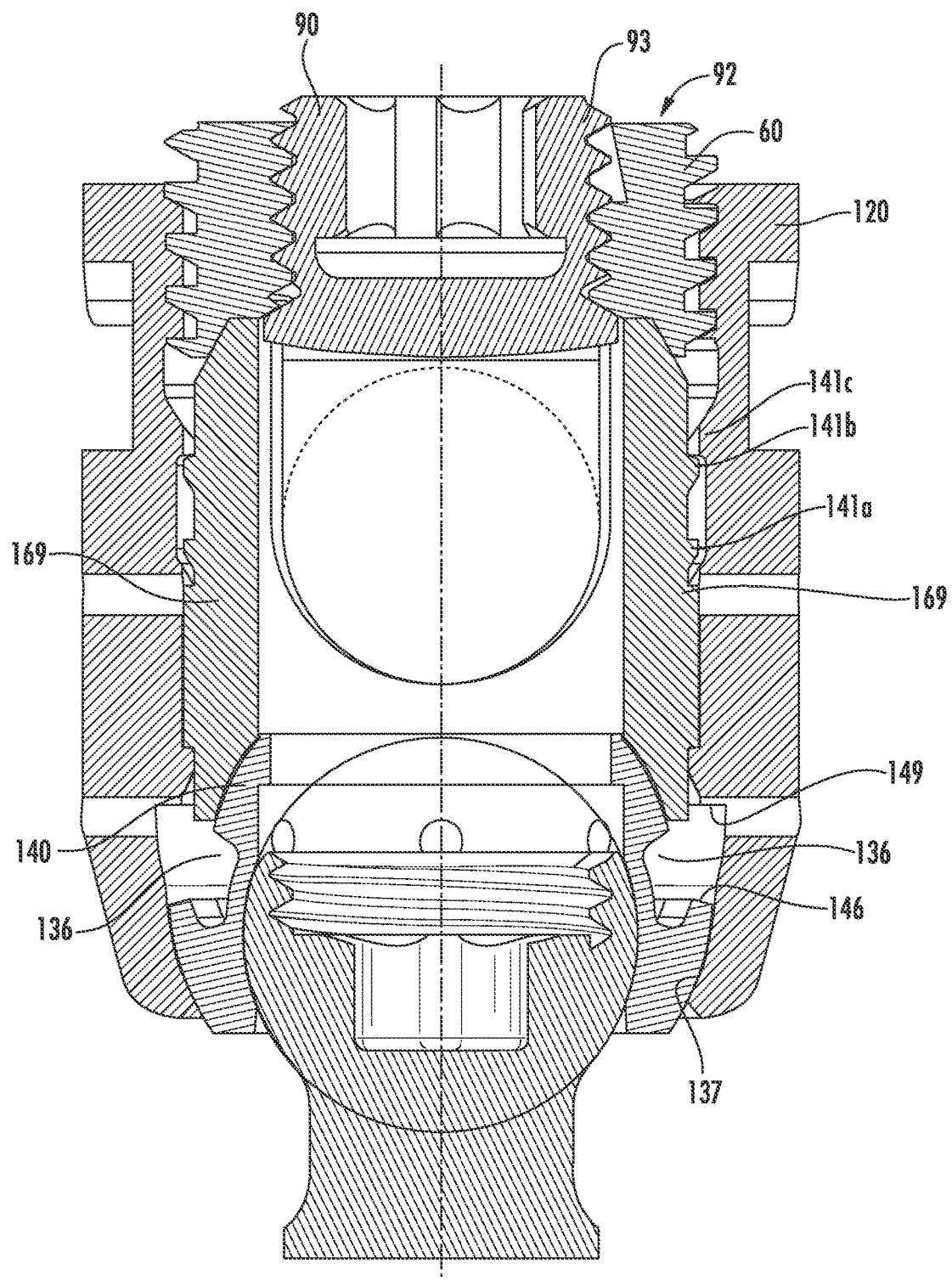
Figure 2F:
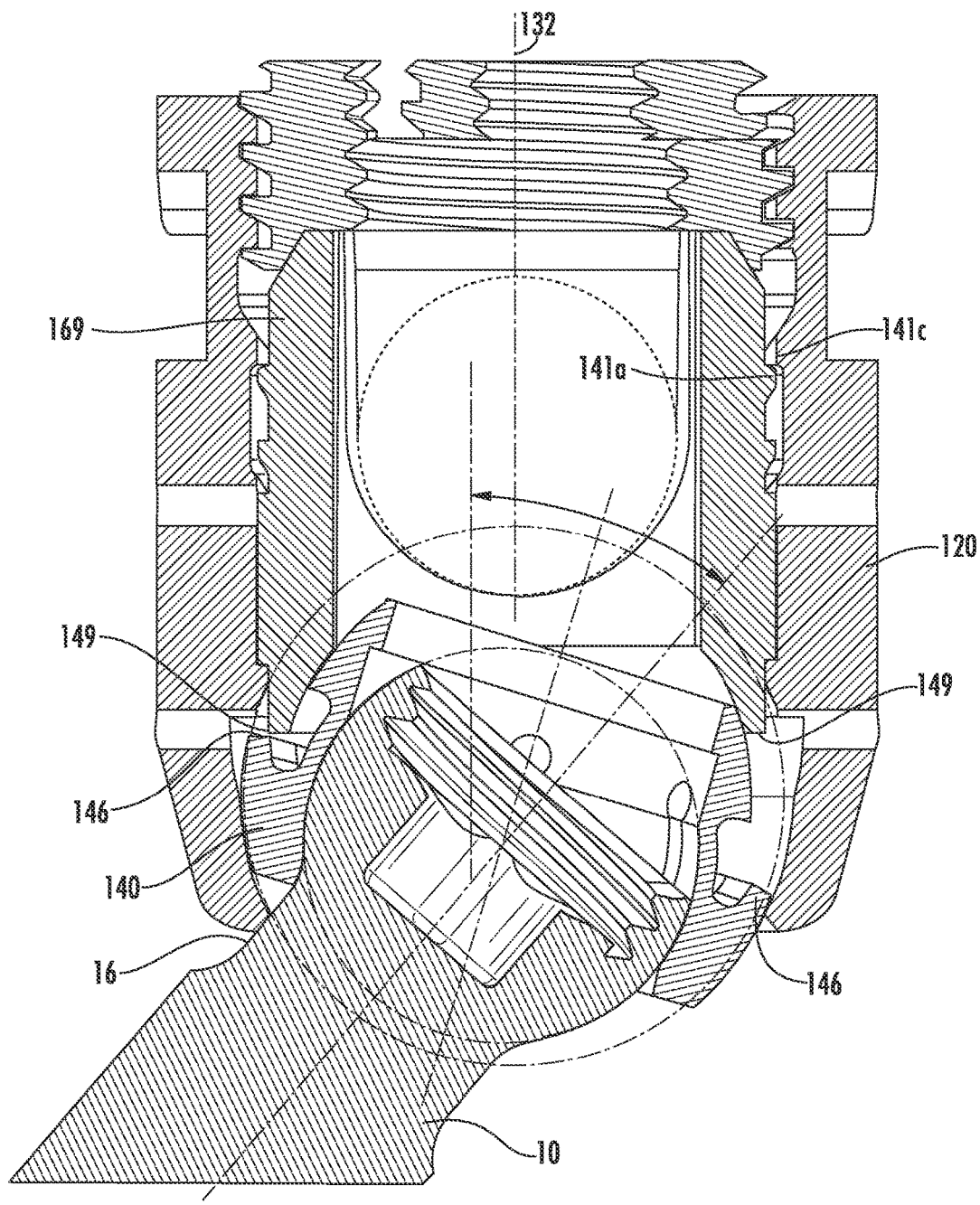

The bushing 140 may thus move within a portion of the axial bore 122 formed in the body 120 between a first (loading/unlocked) position (FIGS. 2A and 2D) and a second (loaded/locked) position (FIGS. 2E-2F). That is, the bushing 140 is moveable within the body 120 between a first position where the bone anchor 10 can be connected to or unconnected from the bushing 140, and the second position where the bushing 140 is locked with respect to the bone anchor 10. The lower end portion 136 of the bushing 140 preferably includes an interior cavity 151 that has a predetermined size to receive and secure the head 14 of the bone anchor 10 so that the bone anchor 10 can rotate polyaxially through a range of angles with respect to the bushing 140 and hence with respect to the body 120 when in an unlocked or loading/unloading position, as shown in FIG. 2F.

As with be described below with reference to FIGS. 4A-4D, the interior cavity 151 formed in the bushing 140 may have a curvate or semi-spherical shape for receiving the curvate or semi-spherical head 14 of the bone anchor 10. The interior cavity 151 formed in the bushing 140 may be constructed so that the bone anchor 10 can polyaxially rotate with respect to the bushing 140, when the bushing is in an unlocked position, and hence, with respect to the body 20. The bushing 140 preferably also includes one or more slots 144 extending from the lower end portion 146 thereof so that at least a portion of the bushing 140 is radially expandable so that the head 14 of the bone anchor 10 can be inserted through the lower opening 142 in the lower end portion 146 and into the interior cavity 151 of the bushing 140 and/or radially compressible to compress or lock against the head 14 of the bone anchor 10 when radial forces are applied thereto. In an implementation, the slots 144 define a plurality of flexible arms 145. The slots 144 may extend from the lower end 146, the upper end 147 or both ends 146, 147. One slot 142 may extend the length of the bushing 140 creating a compressible spring clip.

To interconnect or attach the bone anchor 10 to the body 120, the body 120 may be provided with the bushing 140 pre-assembled and in the loading position, as shown in FIG. 2A. A lower tooth 141a of the saddle 169 engages a tooth 41c of the body in the locking mechanism 138. The lower surface 173 of the saddle 169 contacts the upper surface 172 of the bushing 140. The head 14 of the bone anchor 10 is inserted into the lower opening 24 of the body 20 and into the interior cavity 51 of the bushing 40. As shown in FIG. 2D, the head 14 is further inserted into the interior cavity 151 of the bushing 140, the head 14 engages the interior surfaces of flexible arms 145. Thus, the head 14 is "snapped-in" to the bushing 140 as the flexible arms 145 frictionally retain the head 14 within the cavity 151.

As shown in FIG. 2E, after the head 14 of the bone anchor 10 is fully inserted into the cavity 151 of the bushing 140, a tool may push down on the saddle 169 to push the bushing 140 further within the lower chamber 136 of the body 120 to prevent the head 14 of the bone anchor 10 from becoming dislodged from bushing 140. The downward movement causes the saddle 169 causes the tooth 141b to engage the tooth 141c of the body 120. The downward movement also causes the bushing 140 to lock the head 14 of the bone anchor 10 within the cavity 151. As the bushing 140 moves downward by force of the saddle 169, the arms 145 of the bushing 140 come into contact with the one or more lower chamber surfaces 137 in the lower chamber 136 of the body 120, which exert a force against the arms 145 of the bushing 140, causing the arms 145 to be urged around the head 14 of the bone anchor 10 into a locking position, thereby locking the position of the bone anchor 10 relative to the body 120.

Referring to FIG. 2F, when the bone anchor 10 is in the locked position the head 14 is rotatable within the cavity 151. As illustrated, the bushing 140 of the second implementation, provides for approximately 41° of angulation in each direction with respect to the longitudinal axis 32, as both the head 14 and the bushing 140 are rotatable within the lower chamber 136 of the body 120. As illustrated, the neck portion 16 acts as a stop as it contacts the lower end 134 of the bushing 140. Alternatively, the bushing 140 further includes wings 146 that contact ledges 149 of the saddle 169 that may act as a stop to limit the rotational movement of the bushing 140 within the interior cavity 151.

Referring to FIG. 2F, the locking cap 92 is movable from an unlocked to a locked position to lock the bone anchor 10 and the rod (not shown) in place within the body 20. The locking cap of FIG. 2F operates in substantially the same manner as the locking cap described with reference to FIG. 1C.

Thus, the above provides for implementations of a bone fixation assembly that provide for easy securing of the bone anchor within the assembly and for polyaxial rotation of the bone anchor within the bone fixation assembly. In the first and second embodiments, the interaction of the bone anchor, bushing and body have specifically designed sections thereof that come into contact to secure the bone anchor within the bushing. These interactions are further detailed with reference to FIGS. 3-16.

With reference to FIGS. 3A-3E, various configurations of the body 20/120 will now be described. As illustrated, the body may be have the lower end formed as having one of several shapes that may interact with the bushing 40/140. Various configurations of the bushing 40/140 will be introduced in FIGS. 4A-4D. The cooperative engagement of the several configurations of the body 20/120 and the bushing 40/140 are illustrated in FIGS. 5-16.

Figure 3A:
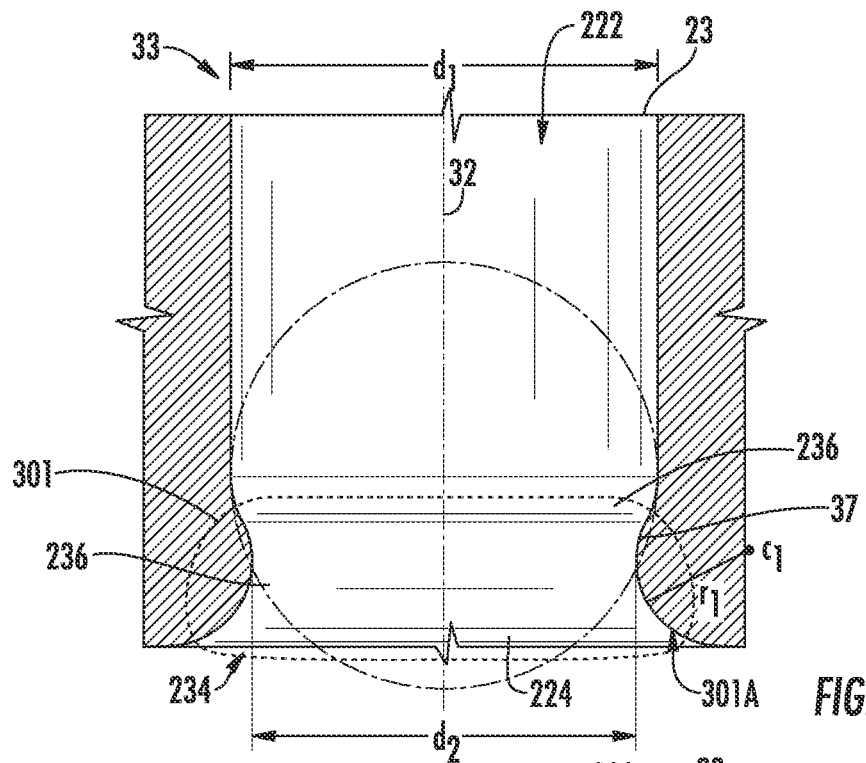

FIG. 3A illustrates a first embodiment of the body 20/120 having a convex lower end 234. In particular, the chamber 236 may be formed as a convex region proximate to the lower opening 224 where the convex region 301 may have a radius of curvature r1 from a center point c1. Thus, a surface 301A of the circle defined by the radius of curvature r1 defines the lower opening 224 as having the diameter d2. The center point c1 may be selected such that the lower opening 224 may taper inwardly along the surface 301A of the circumference, where the taper is toward the longitudinal axis 232.

Figure 3B:
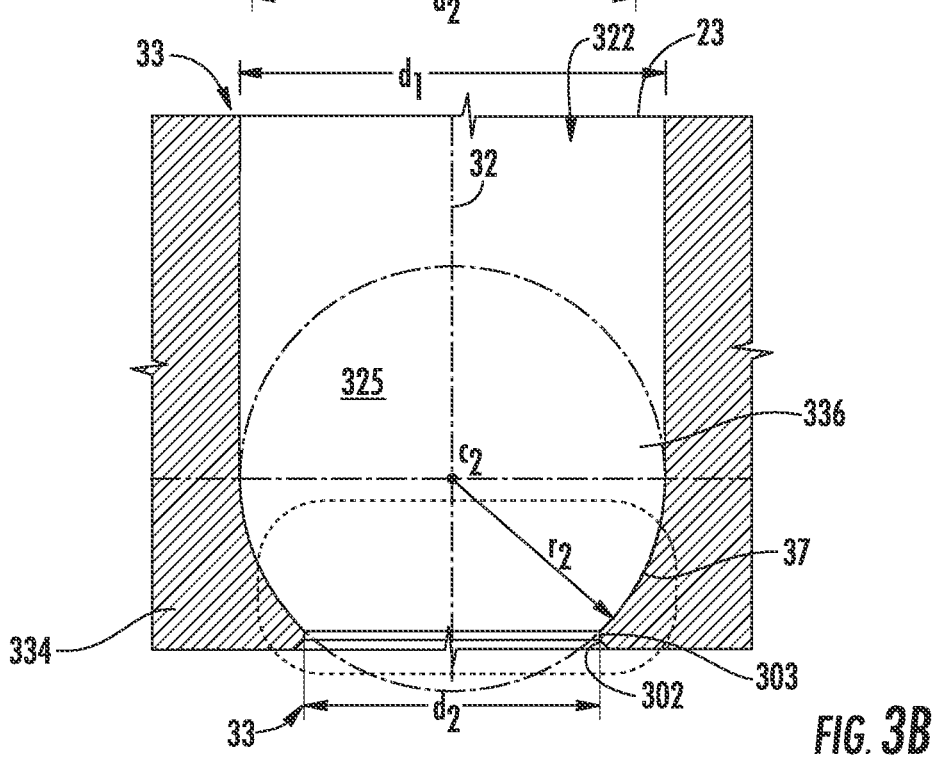

FIG. 3B illustrates a second embodiment of the body 20/120 having a spherical lower end 334. As shown in FIG. 3B, the spherical lower end 334 is formed having a radius r2, as measured from a center point c2 at the longitudinal axis 232. Thus, a spherical region 325 is created within the chamber 336 of the body 20/120 that has a center c2. The lower end 334 may include a tapered region 302 that tapers inwardly to a flat surface 303 that defines the diameter d2 of the lower end 334.

As shown in FIG. 3C, a third embodiment of the body 20/120 having a spherical lower end 334. As shown in FIG. 3C, the spherical lower end 334 is formed having the radius r2, as measured from a center point c2 at the longitudinal axis 232. However, the center point c2 is at location that is shifted upwardly within the chamber 336 of the body 20/120 as compared with the center point c2 in the body 320 of FIG. 3B. Thus, the tapered region 302 that tapers inwardly to the flat surface 303 may be larger than that of FIG. 3B. In accordance with FIG. 3C, the center point c2 may be shifted longitudinally anywhere along the longitudinal axis 232 within the body 20/120.

Alternatively or additionally, as shown in FIGS. 3D and 3E, a non-spherical region 425 within a chamber 446 and having a center c2. The region 425 may be shifted laterally within the body 20/120 such that is at a point along a line that is perpendicular to the longitudinal axis 232. For example, in FIG. 3D the center c2 is shifted to the left of the longitudinal axis 232 (negative), whereas in FIG. 3E, the center c2 is shifted to the right of the longitudinal axis 232 (positive).

Although the body has been explained as having a spherical or non-spherical shape, other shapes may be provided, such as, but not limited to, a conical shape, a torus-like shape, a concave shape or a convex shape.

Figure 4A:
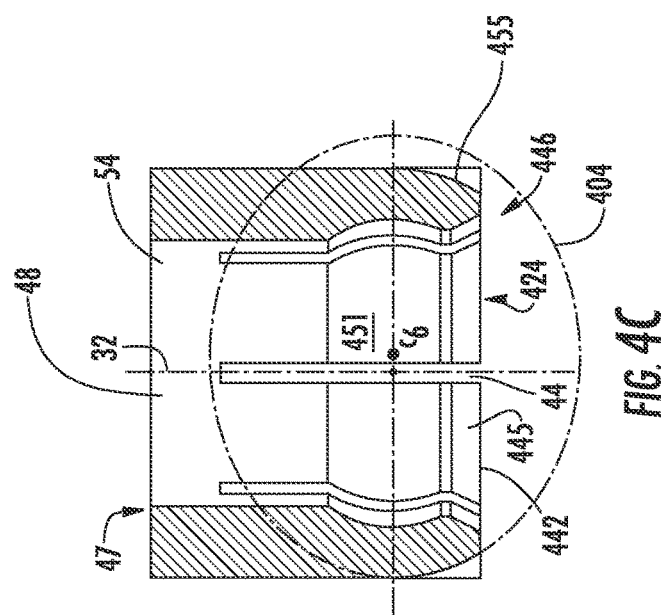
FIGS. 4A-4D illustrate various configurations of a bushing of the bone anchor assembly.

With reference to FIGS. 4A-4D, there is illustrated various configurations of the bushing 40/140. FIG. 4A illustrates a first embodiment of the bushing 240. In the first embodiment, the bushing 240 is provided having a spherical exterior surface 255, which may be sized and configured to contact the lower chamber surfaces of the body. As shown in FIG. 4A, the spherical exterior surface 255 may be defined as portion of a sphere 401 having a radius r4 extending from a center point c4 of a lower end portion 246. The lower end portion 246 includes a lower opening 242 and defines an interior cavity 251 for receiving and securing the head of the bone anchor so that the bone anchor can rotate polyaxially through a range of angles with respect to the bushing 240.

Figure 4B:
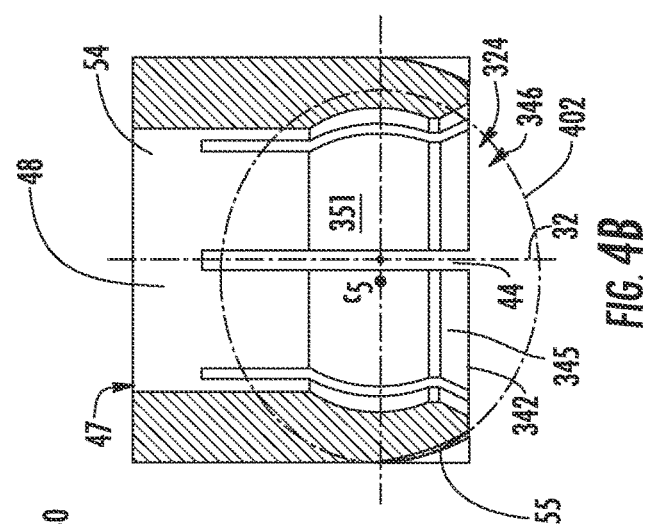

FIG. 4B illustrates a second embodiment of the bushing 340 that includes a non-spherical exterior surface 355, which may be sized and configured to contact the lower chamber surfaces of the body. In the embodiment of FIG. 4B, the non-spherical surface 355 is defined by a non-spherical shape 402 having a center c5 that may be shifted to the left of the longitudinal axis 32 (negative). A lower end portion 346 of the bushing 340 includes an interior cavity 351 for receiving and securing the head of the bone anchor through a lower opening 342 so that the bone anchor can rotate polyaxially through a range of angles with respect to the bushing 340.

Figure 4C:
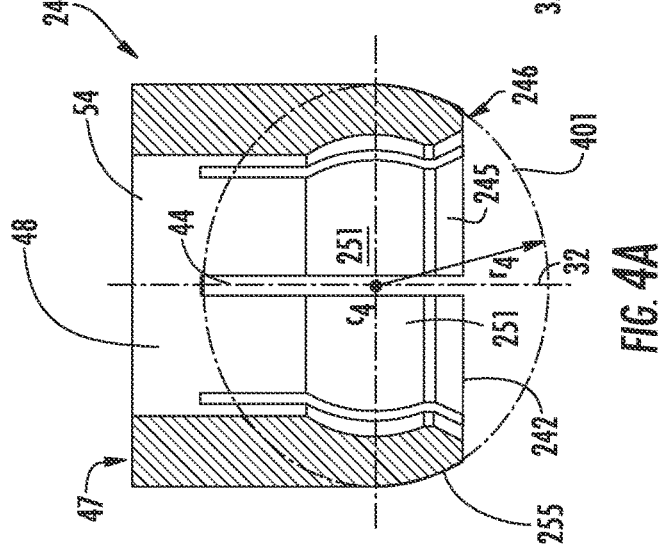

FIG. 4C illustrates a third embodiment of the bushing 440 that includes a non-spherical exterior surface 455, which may be sized and configured to contact the lower chamber surfaces of the body. In the embodiment of FIG. 4C, the center c6 of the non-spherical exterior 455 is shifted to the right of the longitudinal axis 32 (positive). A lower end portion 446 of the bushing 440 includes an interior cavity 451 for receiving and securing the head of the bone anchor through a lower opening 442 so that the bone anchor can rotate polyaxially through a range of angles with respect to the bushing 440.

Figure 4D:
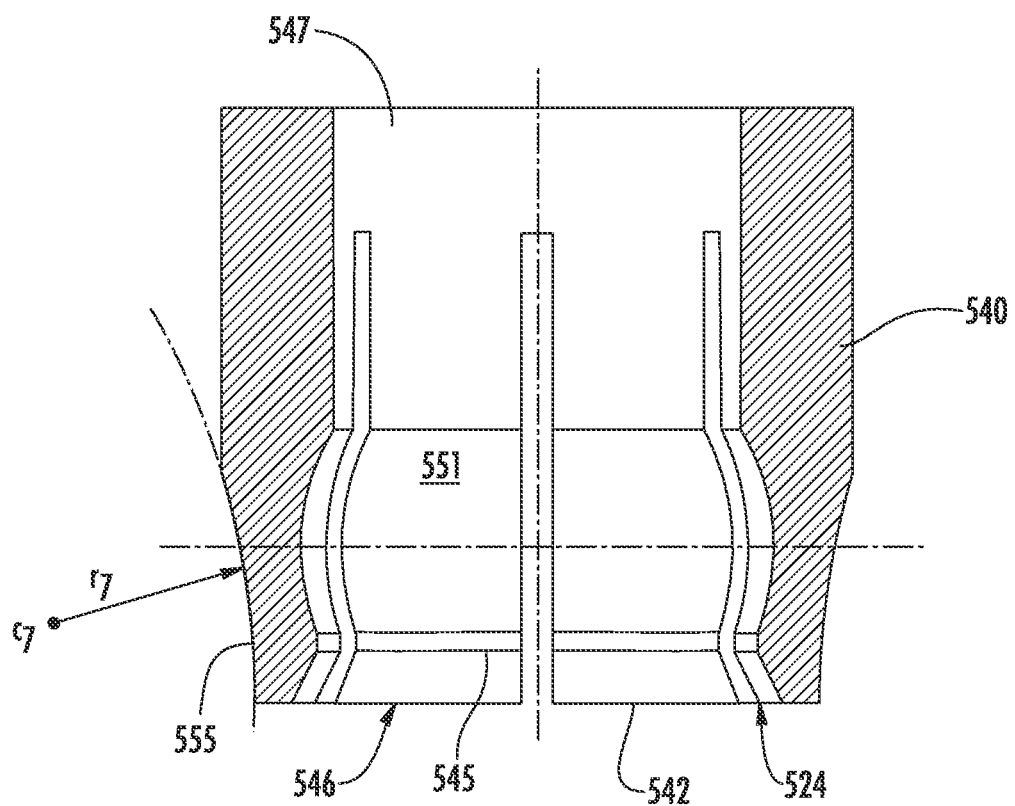

FIG. 4D illustrates a fourth embodiment of the bushing 540 that includes a concave exterior surface 555, which may be sized and configured to contact the lower chamber surfaces of the body. The concave exterior surface 555 may be formed having a radius of curvature r7 as measured from a point c7 outside the bushing 540. A lower end portion 546 of the bushing 540 includes an interior cavity 551 for receiving and securing the head of the bone anchor through a lower opening 542 so that the bone anchor can rotate polyaxially through a range of angles with respect to the bushing 540.

For each of the embodiments of the body 20/120 and bushing 40/140 above, the interactions of the exterior surface of the bushing 40/140 and the lower chamber surfaces 37 of the body 20/120 is described below in greater detail. In particular, In accordance with the geometries disclosed in FIGS. 3A-3E and 4A-4D, the various bushings and bodies may be assembled, as shown in FIGS. 1 and 2 to provide interface geometries between the bushing lower exterior surface portions 255, 355, 455 and 555 and the lower chamber surfaces 37 that assume a partially spherical-to-partially spherical interface as well as a linear taper-to-linear taper interface in order to allow the compression of the bushing interior cavity 51 to thereby lock the position and angulation of the bone anchor is locked with respect to the body 20/120 and polyaxial bone fixation assembly 100 as a locking cap is advanced downward through the body 20/120, urging the spinal rod and the bushing disposed therein downward through the body 120 as well. Table 1, below, sets for the example configurations of the body 20/120 and bushing 40/140.

TABLE 1

Figure 5A:
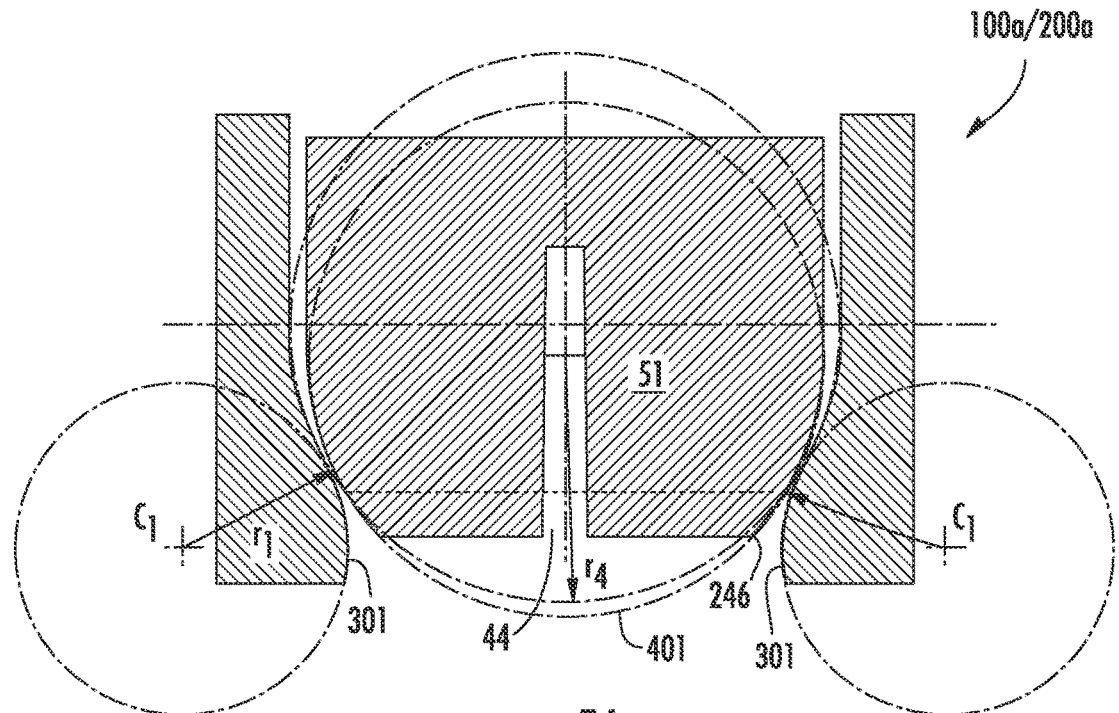
FIGS. 5A-5B illustrate a front sectional view of a first embodiment of a polyaxial pedicle screw assembly of the present disclosure.
Figure 5B:
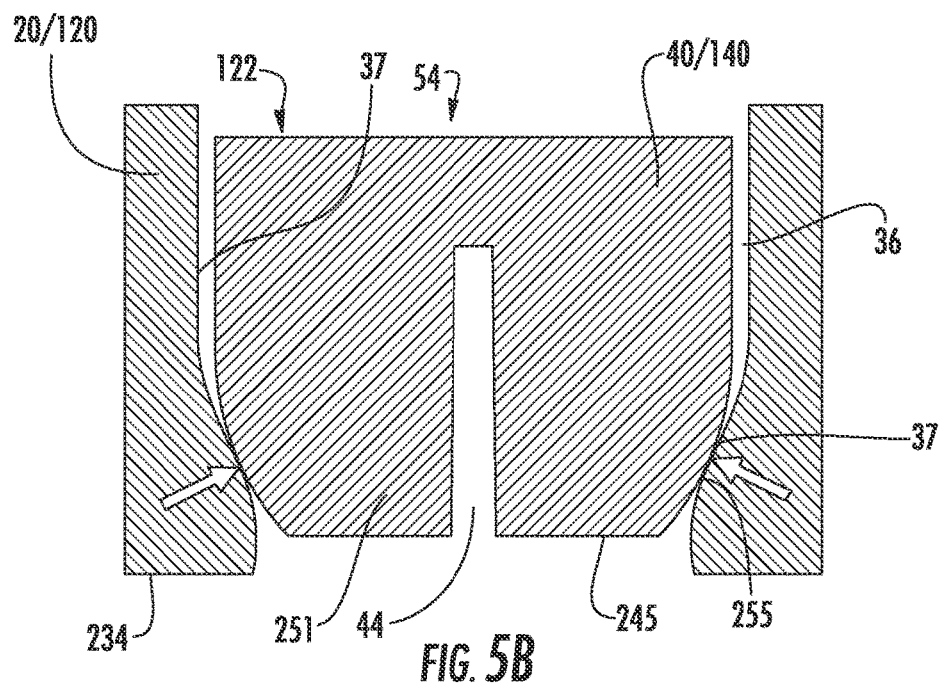
Figure 6A:
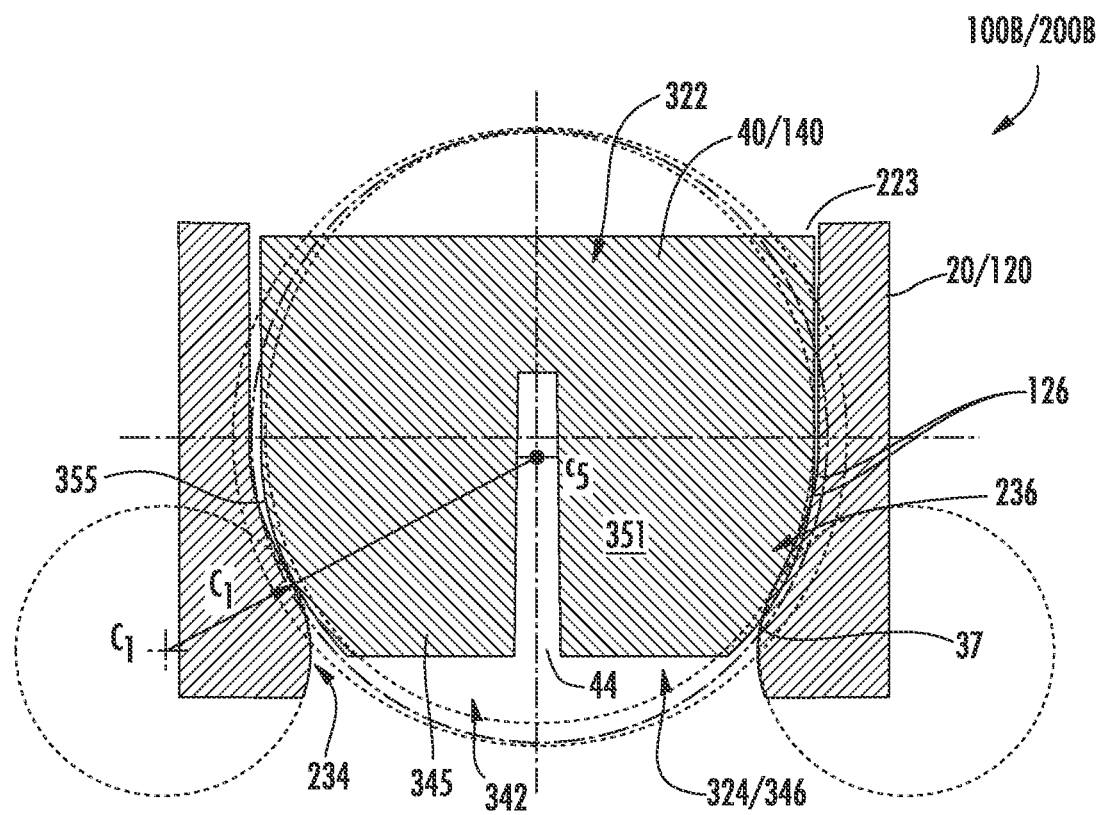
FIGS. 6A-6B illustrate a front sectional view of a second embodiment of a polyaxial pedicle screw assembly of the present disclosure.
Figure 6B:
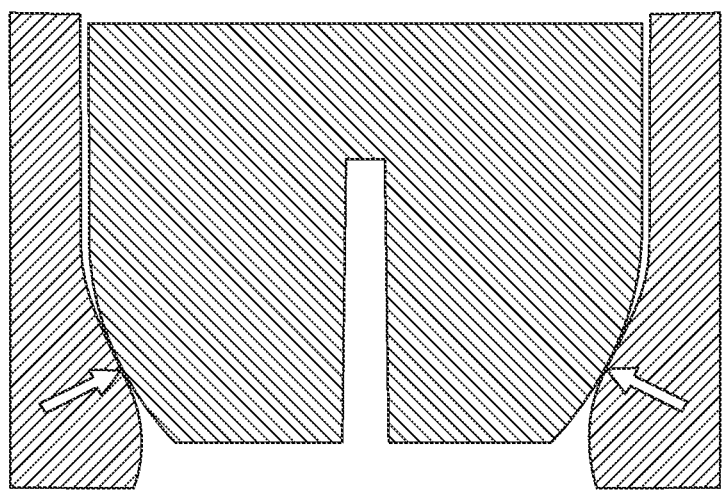
Figure 7A:
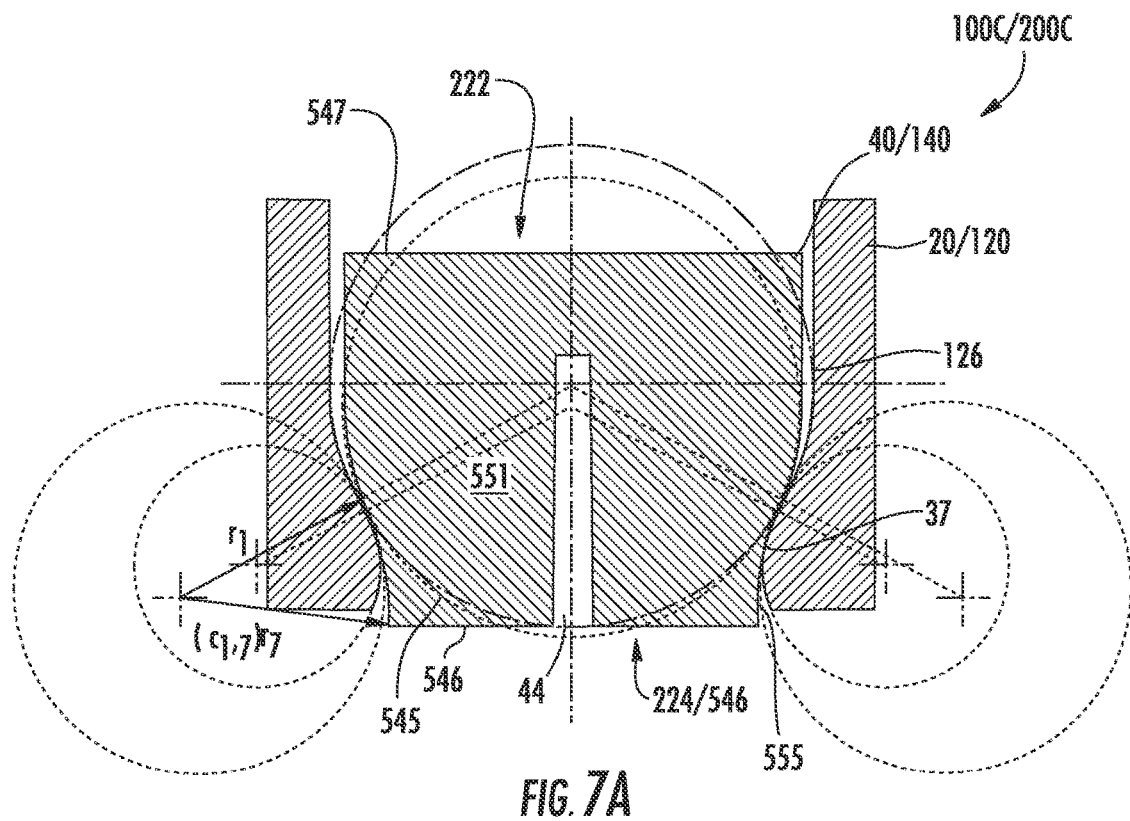
FIGS. 7A-7B illustrate a front sectional view of a third embodiment of a polyaxial pedicle screw assembly of the present disclosure.
Figure 7B:
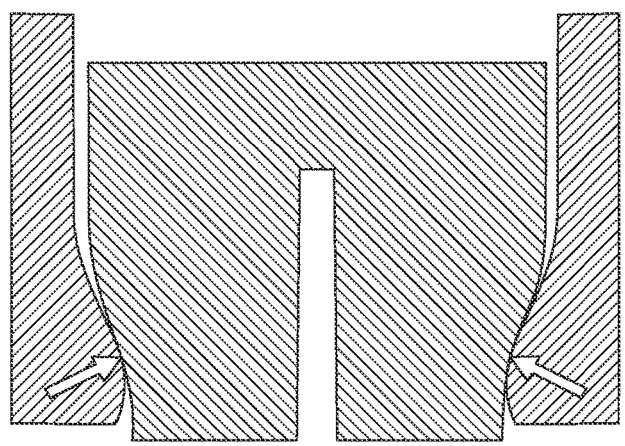
Figure 8A:
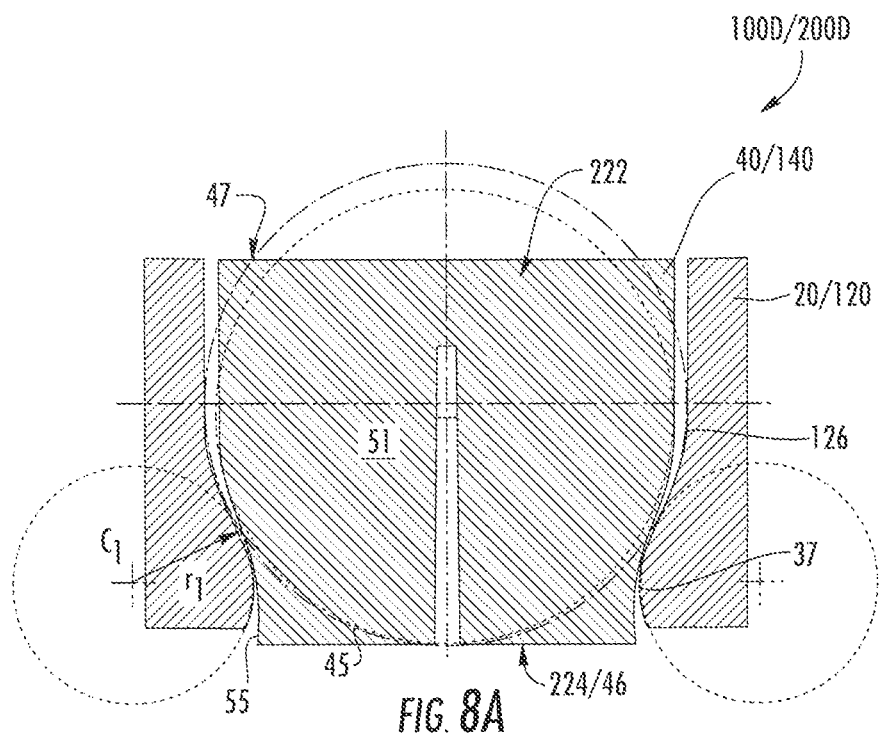
FIGS. 8A-8B illustrate a front sectional view of a fourth embodiment of a polyaxial pedicle screw assembly of the present disclosure.
Figure 8B:
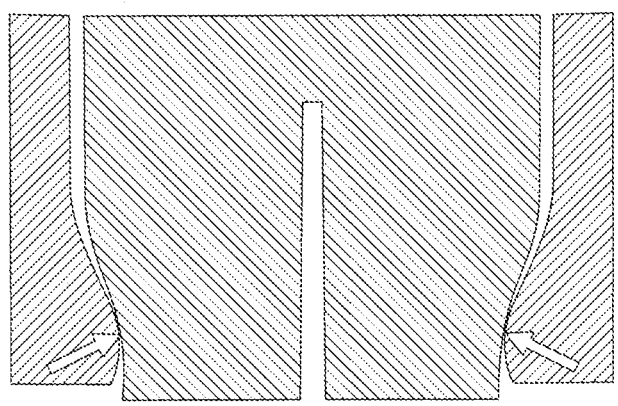
Figure 9A:
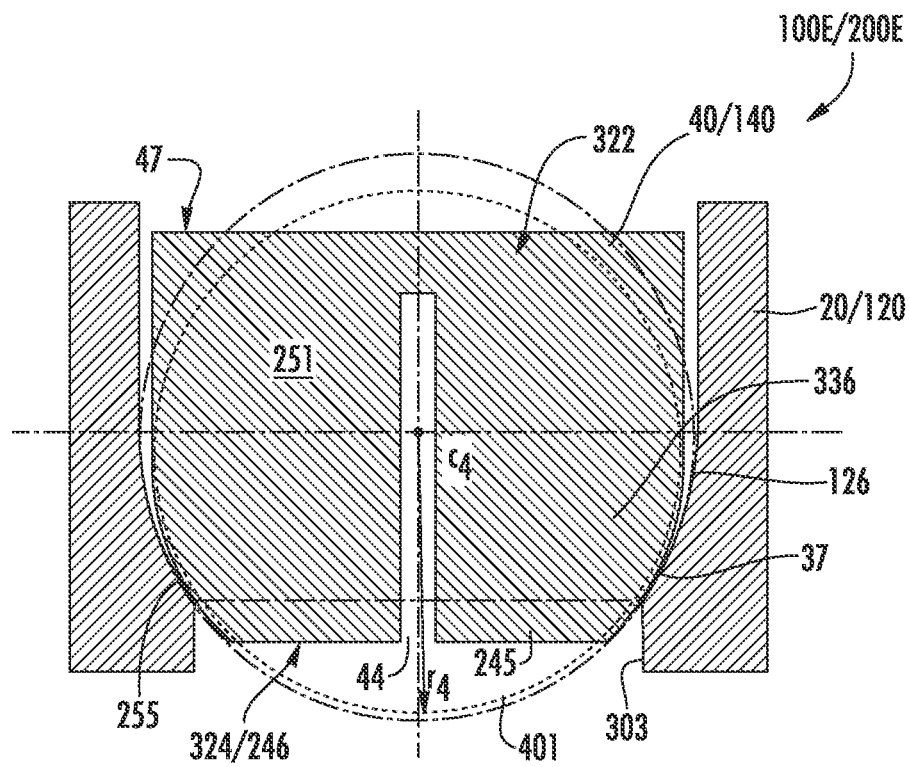
FIGS. 9A-9B illustrate a front sectional view of a fifth embodiment of a polyaxial pedicle screw assembly of the present disclosure.
Figure 9B:
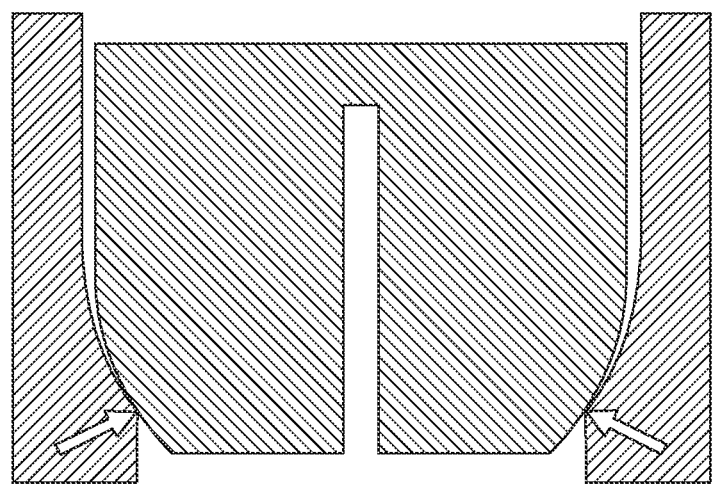
Figure 10A:
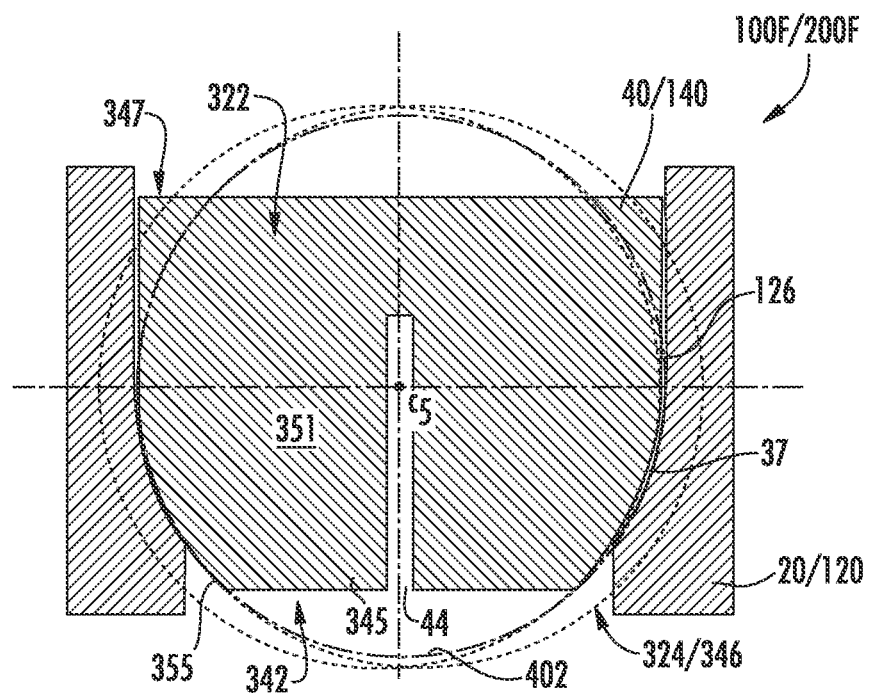
FIGS. 10A-10B illustrate a front sectional view of a sixth embodiment of a polyaxial pedicle screw assembly of the present disclosure.
Figure 10B:
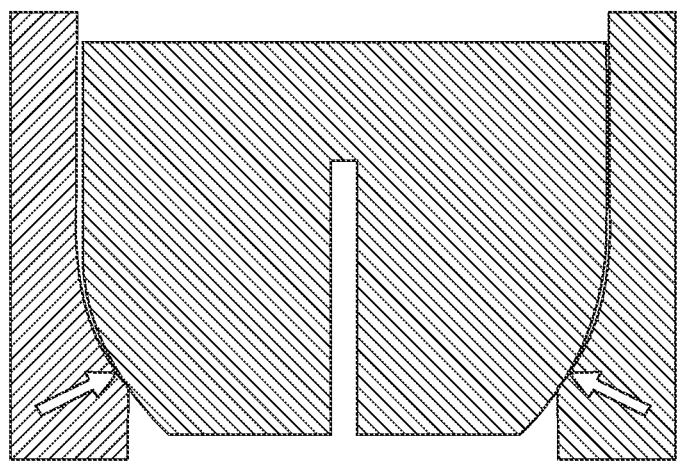
Figure 11A:
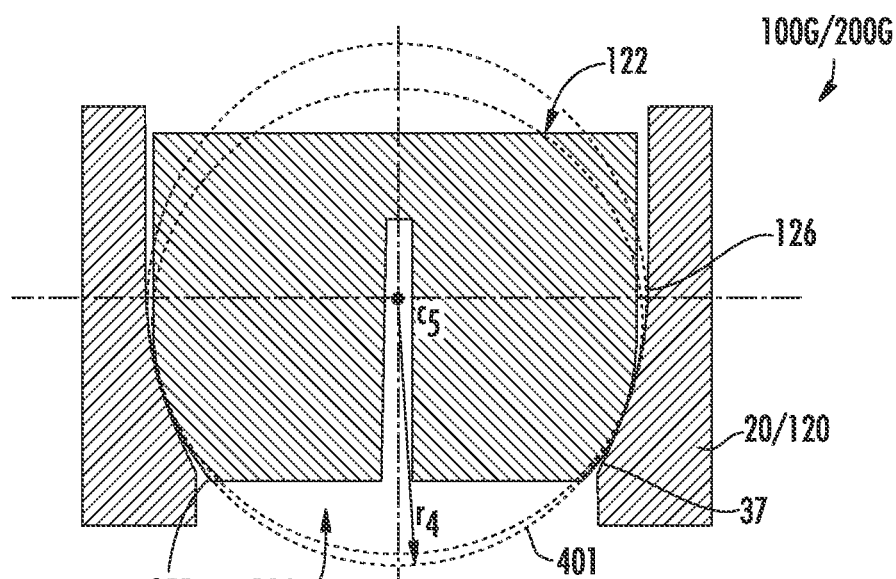
FIGS. 11A-11B illustrate a front sectional view of a seventh embodiment of a polyaxial pedicle screw assembly of the present disclosure.
Figure 11B:
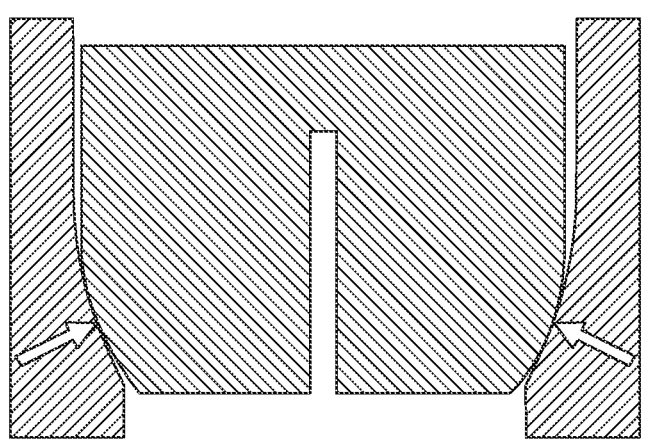
Figure 12A:
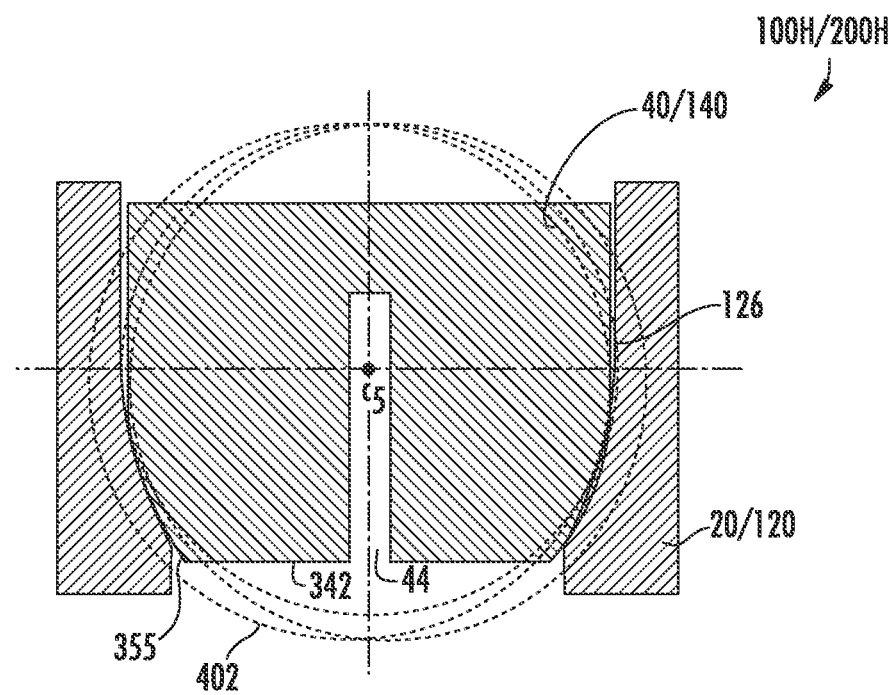
FIGS. 12A-12B illustrate a front sectional view of an eighth embodiment of a polyaxial pedicle screw assembly of the present disclosure.
Figure 12B:
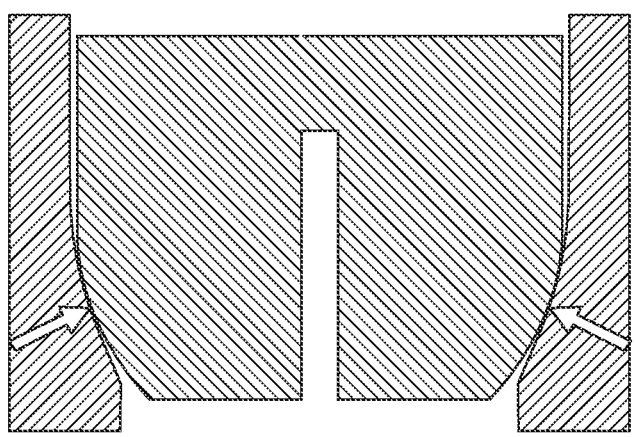
Figure 13:
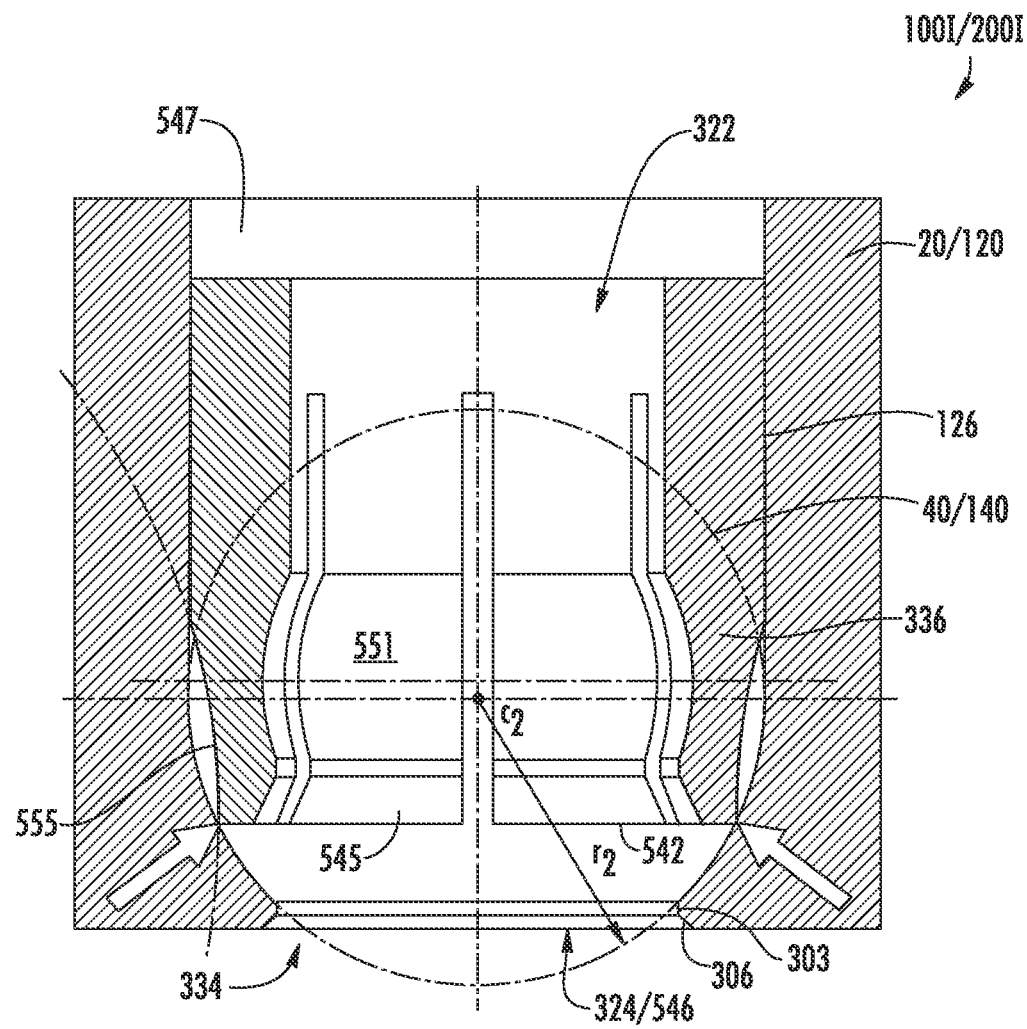
FIG. 13 illustrates a front sectional view of an eighth embodiment of a polyaxial pedicle screw assembly of the present disclosure.
Figure 14:
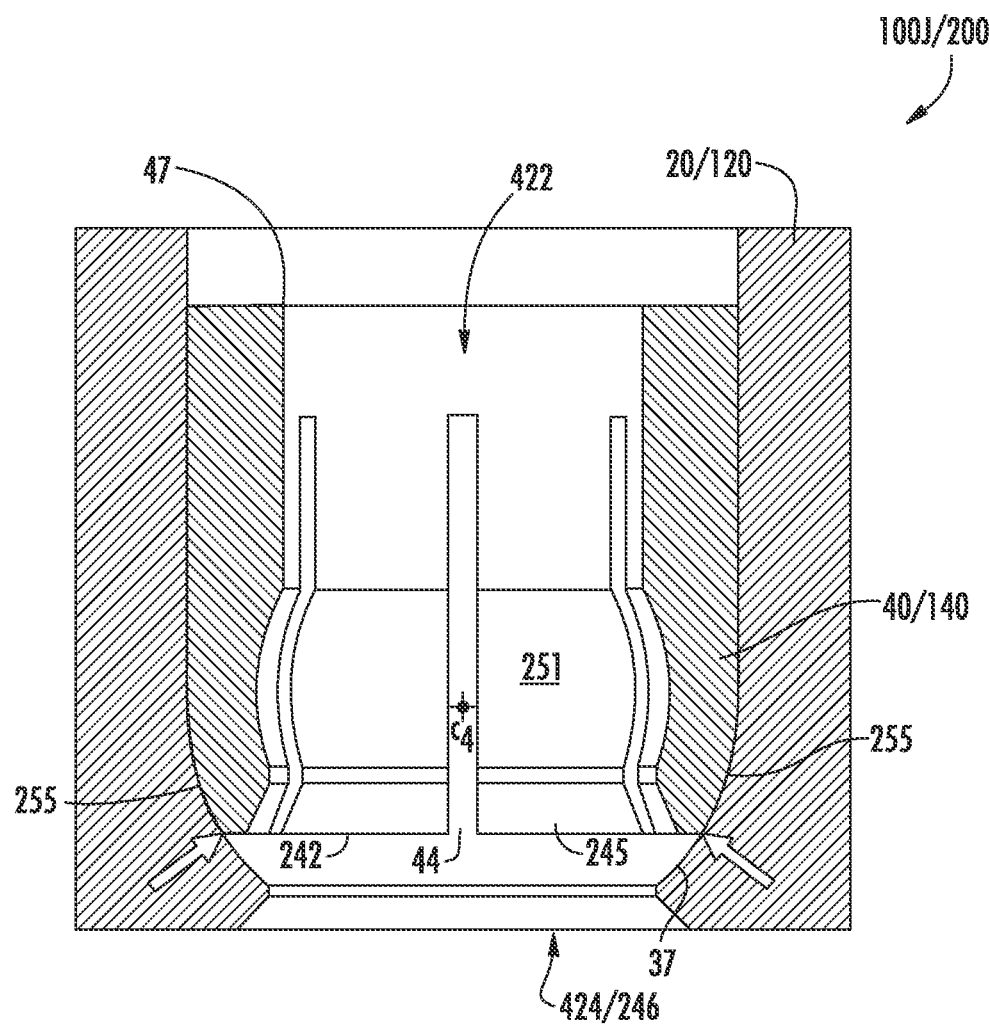
FIG. 14 illustrates a front sectional view of an ninth embodiment of a polyaxial pedicle screw assembly of the present disclosure.
Figure 15A:
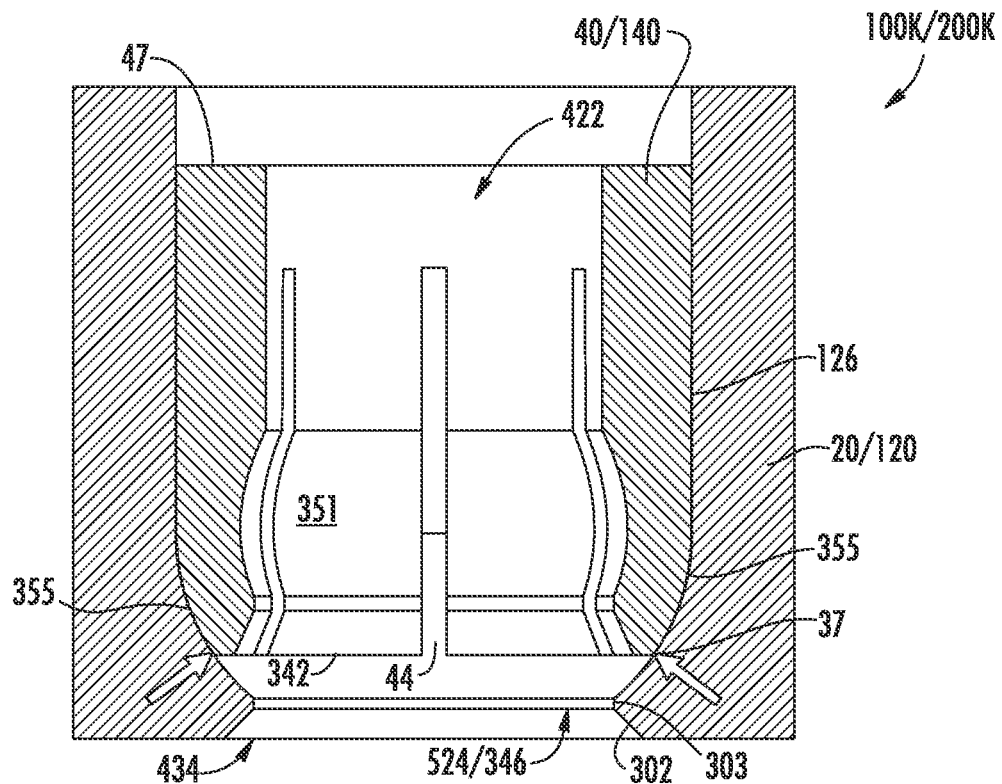
FIGS. 15A-15B illustrate a front sectional view of an tenth embodiment of a polyaxial pedicle screw assembly of the present disclosure.
Figure 15B:
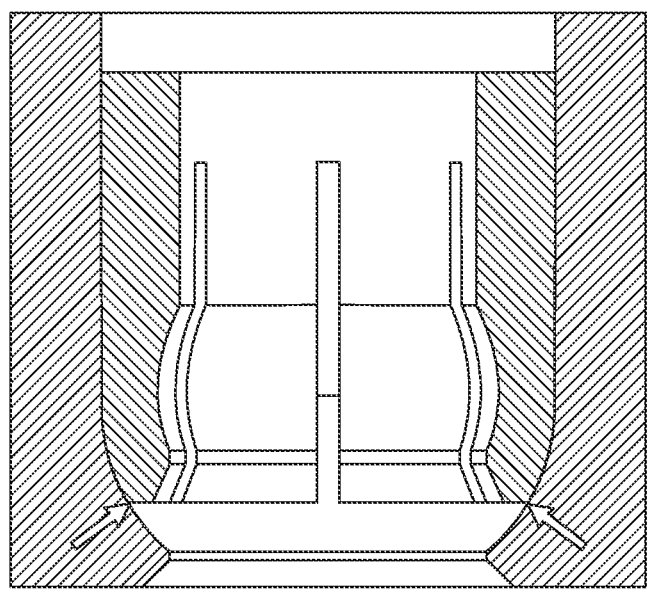

| Polyaxial Pedical Screw Interface Body/Bushing Matrix | | | Body 20/120 | | | |
|---|---|---|---|---|---|---|
| | | | Convex | Concave | | |
| | | | torus-like (FIG. 3A) | spherical (FIGS. 3B-3C) | torus-like (FIGS. 3D-3E) | Conical |
| Bushing 40/140 | convex | spherical (FIG. 4A) | FIGS. 5A-5B | FIGS. 9A-9B | FIG. 14 | FIGS. 11A-11B |
| | | torus-like (FIGS. 4B-4C) | FIGS. 6A-6B | FIGS. 10A-10B | FIGS. 15A-15B | FIGS. 12A-12B |
| | concave | torus-like (FIG. 4D) | FIGS. 7A-7B | FIG. 13 | FIGS. 16A-16B | |
| | | conical | FIGS 8A-8B | | | |

FIGS. 5A-5B illustrate a front sectional view of a first embodiment of a polyaxial pedicle screw assembly of the present disclosure in which a torus-like convex body lower interior surface portion and a spherical-convex bushing lower exterior surface portion form the bearing surfaces that allow the assembly to be locked FIGS. 5A-5B illustrate a polyaxial bone fixation assembly 100A/200A that includes a body 20/120 having an axial bore characterized by a generally cylindrical interior geometry adjacent the axial bore 122 and characterized by a torus-like convex interior geometry along the lower chamber surfaces 37 adjacent the lower opening 124. More specifically, as can best be seen taking into account the dotted circles of FIG. 5A, the lower chamber surfaces 37 progresses from an essentially cylindrical surface adjacent the body axial bore 122 and transitions through a hemi-concave surface tracing out approximately 45 degrees and smoothly inflects to a hemi-convex surface tracing out approximately 45 degrees adjacent the body lower opening 124.

The bushing 40/140 is characterized by an exterior surface 55 that assumes a generally cylindrical geometry adjacent the upper end 47 and smoothly transitions to a spherical convex geometry or hemi-convex surface along the lower exterior surface portion 255 and adjacent to the lower end 241. As the bushing 40/140 is urged downward through the polyaxial bone fixation assembly 100 and the lower exterior surface portion 255 bears against the lower chamber surfaces 37 of the body 120, the interior cavity 51 is locked around the head of the bone anchor as the flexible arms 45 are drawn together and the position and angulation of the bone anchor is locked with respect to the body 120 and polyaxial bone fixation assembly 100. The dark arrows show in FIG. 5B illustrate a point of contact between the body 20/120 and the bushing 40/140 when in the locked state.

FIGS. 6A-6B illustrate a front sectional view of a second embodiment of a polyaxial pedicle screw assembly of the present disclosure in which a torus-like convex body lower interior surface portion and a torus-convex bushing lower exterior surface portion form the bearing surfaces that allow the assembly to be locked. FIGS. 6A-6B illustrate a polyaxial bone fixation assembly 100B/200B that includes a body 20/120 having an axial bore characterized by a generally cylindrical interior geometry adjacent the axial bore 322 and characterized by a torus-like convex interior geometry at the lower chamber surfaces 37 adjacent the lower end 324. More specifically, as can best be seen taking into account the dotted circles of FIG. 6A, the body interior surface 126 progresses from an essentially cylindrical surface adjacent the body axial bore 222 and transitions through a hemi-concave surface tracing out approximately 45 degrees and smoothly inflects to a hemi-convex surface tracing out approximately 45 degrees adjacent the body lower opening 224.

The bushing 40/140 is characterized by an exterior surface 355 that assumes a generally cylindrical geometry adjacent the upper end 47 and smoothly transitions to a torus-like convex geometry or hemi-convex surface along the lower exterior surface portion 355 and adjacent to the lower end portion 346. As the bushing is urged downward through the polyaxial bone fixation assembly 100B/200B and the lower exterior surface portion 355 bears against the lower chamber surfaces 37 of the body 20/120, the interior cavity 351 is crush locked around the head of the bone anchor as the flexible arms 345 are drawn together and the position and angulation of the bone anchor is locked with respect to the body 20/120 and polyaxial bone fixation assembly 100B/200B. The dark arrows show in FIG. 6B illustrate a point of contact between the body 20/120 and the bushing 40/140 when in the locked state.

FIGS. 7A-7B illustrate a front sectional view of a third embodiment of a polyaxial pedicle screw assembly of the present disclosure in which a torus-like convex body lower interior surface portion and a torus-like concave bushing lower exterior surface portion form the bearing surfaces that allow the assembly to be locked, FIGS. 7A-7B illustrate a polyaxial bone fixation assembly 100C/200C that includes a body 20/120 having an axial bore characterized by a generally cylindrical interior geometry adjacent the axial bore 222 and characterized by a torus-like convex interior geometry at the lower chamber surfaces 37 adjacent the lower opening 224. More specifically, as can best be seen taking into account the dotted circles of FIG. 7A, the body interior surface 126 progresses from an essentially cylindrical surface adjacent the body axial bore 222 and transitions through a hemi-concave surface tracing out approximately 45 degrees and smoothly inflects to a partially-convex surface tracing out approximately 45 degrees adjacent the body lower opening 224.

The bushing 40 is characterized by an exterior surface 555 that assumes a generally cylindrical geometry adjacent the upper end 547 and smoothly transitions to a torus-like concave geometry along the lower exterior surface portion 555 and adjacent the lower end portion 546. As the bushing 40/140 is urged downward through the polyaxial bone fixation assembly 100 and the lower exterior surface portion 555 bears against the lower chamber surfaces 37 of the body 20/120, the interior cavity 551 is crush locked around the head of the bone anchor as the flexible arms 545 are drawn together and the position and angulation of the bone anchor is locked with respect to the body 20/120 and the polyaxial bone fixation assembly 100C/200C. The dark arrows show in FIG. 7B illustrate a point of contact between the body 20/120 and the bushing 40/140 when in the locked state.

FIGS. 8A-8B illustrate a front sectional view of a fourth embodiment of a polyaxial pedicle screw assembly of the present disclosure in which a torus-like convex body lower interior surface portion and a conical bushing lower exterior surface portion form the bearing surfaces that allow the assembly to be locked. FIGS. 8A-8B illustrate a polyaxial bone fixation assembly 100D/200D that includes a body 20/120 having an axial bore characterized by a generally cylindrical interior geometry adjacent the axial bore 222 and characterized by a torus-like convex interior geometry at the lower chamber surfaces 37 adjacent the lower opening 224. More specifically, as can best be seen taking into account the dotted circles of FIG. 8A, the body interior surface 126 progresses from an essentially cylindrical surface adjacent the body axial bore 222 and transitions through a hemi-concave surface tracing out approximately 45 degrees and smoothly inflects to a partially-convex surface tracing out approximately 45 degrees adjacent the body lower opening 224.

The bushing 40/140 is characterized by an exterior surface 55 that assumes a generally cylindrical geometry adjacent the upper end 47 and smoothly transitions through a conical taper along the bushing lower exterior surface portion 55 prior to terminating in a cylindrical geometry adjacent the bushing lower end portion 46. As the bushing 40/140 is urged downward through the polyaxial bone fixation assembly 100C/200D and the conical taper disposed along the lower exterior surface portion 255, 355, 455 and 555 bears against the lower chamber surfaces 37 of the body 20/120, the interior cavity 51 is crush locked around the head of the bone anchor as the flexible arms 45 are drawn together and the position and angulation of the bone anchor is locked with respect to the body 20/120 and the polyaxial bone fixation assembly 100D/200D. The dark arrows show in FIG. 8B illustrate a point of contact between the body 20/120 and the bushing 40/140 when in the locked state.

FIGS. 9A-9B illustrate a front sectional view of a fifth embodiment of a polyaxial pedicle screw assembly of the present disclosure in which a spherical-concave body lower interior surface portion and a spherical-convex bushing lower exterior surface portion form the bearing surfaces that allow the assembly to be locked. FIGS. 9A-9B illustrate a polyaxial bone fixation assembly 100E/200E that includes a body 20/120 having an axial bore characterized by a generally cylindrical interior geometry adjacent the axial bore 322 and terminating in a generally cylindrical interior geometry adjacent the lower opening 324 having a radius smaller than the radius characterizing the axial bore at the axial bore 322. Prior to terminating in the cylindrical geometry at the lower opening 324, the axial bore is characterized by a spherical concave surface geometry along the lower chamber surfaces 37. More specifically, as can best be seen taking into account the dotted circles in FIG. 9A, the body interior surface 126 progresses from an essentially cylindrical surface adjacent the body axial bore 322 and smoothly transitions through a hemi-concave surface along the body lower chamber surfaces 37 tracing out approximately 45 degrees and transitions to an essentially cylindrical surface adjacent the body lower opening 324, the radius of the cylindrical surface adjacent the body lower opening 324 being smaller than the radius of the cylindrical surface adjacent the body axial bore 322.

The bushing 40/140 is characterized by an exterior surface 255 that assumes a generally cylindrical geometry adjacent the upper end 47 and smoothly transitions to a spherical-convex, or hemi-convex, surface along the bushing lower exterior surface portion 255 tracing out an angle of approximately 45 degrees that terminates at the bushing lower end portion 246. As the bushing 40/140 is urged downward through the polyaxial bone fixation assembly 100 and the lower exterior surface portion 255 bears against the lower chamber surfaces 37 of the body 20/120, the interior cavity 251 is crush locked around the head of the bone anchor as the flexible arms 245 are drawn together and the position and angulation of the bone anchor is locked with respect to the body 20/120 and the polyaxial bone fixation assembly 100E/200E. The dark arrows show in FIG. 9B illustrate a point of contact between the body 20/120 and the bushing 40/140 when in the locked state.

FIGS. 10A-10B illustrate a front sectional view of a sixth embodiment of a polyaxial pedicle screw assembly of the present disclosure in which a spherical-concave body lower interior surface portion and a torus-like convex bushing lower exterior surface portion form the bearing surfaces that allow the assembly to be locked. FIGS. 10A-10B illustrate a polyaxial bone fixation assembly 100F/200F that includes a body 20/120 having an axial bore characterized by a generally cylindrical interior geometry adjacent the axial bore 322 and terminating in a generally cylindrical interior geometry adjacent the lower opening 324 having a radius smaller than the radius characterizing the axial bore at the axial bore 322. Prior to terminating in the cylindrical geometry at the lower opening 324, the axial bore is characterized by a spherical concave surface geometry along the lower chamber surfaces 37. More specifically, as can best be seen taking into account the dotted circles in FIG. 10A, the body interior surface 126 progresses from an essentially cylindrical surface adjacent the body axial bore 322 and smoothly transitions through a hemi-concave surface along the body lower chamber surfaces 37 tracing out approximately 45 degrees and transitions to an essentially cylindrical surface adjacent the body lower opening 324, the radius of the cylindrical surface adjacent the body lower opening 324 being smaller than the radius of the cylindrical surface adjacent the body axial bore 322.

The bushing 40/140 is characterized by an exterior surface 355 that assumes a generally cylindrical geometry adjacent the bushing upper end 347 and smoothly transitions to a torus-like convex, or hemi-convex, surface along the bushing lower exterior surface portion 355 tracing out an angle of approximately 45 degrees that terminates at the bushing lower end portion 346. As the bushing is urged downward through the polyaxial bone fixation assembly 100F/200F and the lower exterior surface portion 355 bears against the lower chamber surfaces 37 of the body 20/120, the interior cavity 351 is crush locked around the head of the bone anchor as the flexible arms 345 are drawn together and position and angulation of the bone anchor is locked with respect to the body 20/120 and the polyaxial bone fixation assembly 100F/200F. The dark arrows show in FIG. 10B illustrate a point of contact between the body 20/120 and the bushing 40/140 when in the locked state.

FIGS. 11A-11B illustrate a front sectional view of a seventh embodiment of a polyaxial pedicle screw assembly of the present disclosure in which a conical body lower interior surface portion and a spherical-convex bushing lower exterior surface portion form the bearing surfaces that allow the assembly to be locked. FIGS. 11A-11B illustrate a polyaxial bone fixation assembly 100G/200G that includes a body 20/120 having an axial bore characterized by a generally cylindrical interior geometry adjacent the axial bore 122 and terminating in a cylindrical interior geometry adjacent the lower opening 124 having a radius smaller than the radius characterizing the axial bore at the axial bore 122. Prior to terminating in the cylindrical geometry at the lower opening 124, the axial bore is characterized by a conical surface geometry that provides a linear taper along the lower chamber surfaces 37. More specifically, as can best be seen taking into account the dotted circles in FIG. 11A, the body interior surface 126 progresses from an essentially cylindrical surface adjacent the body axial bore 122 and transitions to a conical surface geometry along the body lower chamber surfaces 37 and transitions back to an essentially cylindrical surface adjacent the body lower opening 124, the radius of the cylindrical surface adjacent the body lower opening 124 being smaller than the radius of the cylindrical surface adjacent the body axial bore 122.

The bushing 40/140 is characterized by an exterior surface 255 that assumes a generally cylindrical geometry adjacent the upper end 47 and smoothly transitions to a spherical-convex, or hemi-convex, surface along the bushing lower exterior surface portion 255 tracing out an angle of approximately 45 degrees that terminates at the bushing lower end portion 246. As the bushing 40/140 is urged downward through the polyaxial bone fixation assembly 100G/200G and the bushing lower exterior surface portion 255 bears against the body lower chamber surfaces 37, the interior cavity 251 is crush locked around the head of the bone anchor as the flexible arms 245 are drawn together and the position and angulation of the bone anchor is locked with respect to the body 20/120 and the polyaxial bone fixation assembly 100G/200G. The dark arrows show in FIG. 11B illustrate a point of contact between the body 20/120 and the bushing 40/140 when in the locked state.

FIGS. 12A-12B illustrate a front sectional view of an eighth embodiment of a polyaxial pedicle screw assembly of the present disclosure in which a conical body lower interior surface portion and a torus-like convex bushing lower exterior surface portion form the bearing surfaces that allow the assembly to be locked. FIGS. 12A-12B illustrate a polyaxial bone fixation assembly 100H/200H that includes a body 20/120 having an axial bore characterized by a generally cylindrical interior geometry adjacent the axial bore 122 and terminating in a cylindrical interior geometry adjacent the lower opening 124 having a radius smaller than the radius characterizing the axial bore at the axial bore 122. Prior to terminating in the cylindrical geometry at the lower opening 124, the axial bore is characterized by a conical surface geometry that provides a linear taper along the lower chamber surfaces 37. More specifically, as can best be seen taking into account the dotted circles in FIG. 12A, the body interior surface 126 progresses from an essentially cylindrical surface adjacent the body axial bore 122 and transitions to a conical surface geometry along the body lower chamber surfaces 37 and transitions back to an essentially cylindrical surface adjacent the body lower opening 124, the radius of the cylindrical surface adjacent the body lower opening 124 being smaller than the radius of the cylindrical surface adjacent the body axial bore 122.

The bushing 40/140 is characterized by an exterior surface 355, 455 that assumes a generally cylindrical geometry adjacent the bushing upper end 47 and smoothly transitions to a torus-like convex, or hemi-convex, surface along the lower exterior surface portion 355 tracing out an angle of approximately 45 degrees that terminates at the bushing lower end portion 346, 446. As the bushing 40/140 is urged downward through the polyaxial bone fixation assembly 100H/200H and the bushing lower exterior surface portion 355 bears against the lower chamber surfaces 37, the interior cavity 351, 451 is crush locked around the head of the bone anchor as the flexible arms 345, 445 are drawn together and the position and angulation of the bone anchor is locked with respect to the body 20/120 and the polyaxial bone fixation assembly 100H/200H. The dark arrows show in FIG. 12B illustrate a point of contact between the body 20/120 and the bushing 40/140 when in the locked state.

FIG. 13 illustrates a polyaxial bone fixation assembly 100I/200I that includes a body 20/120 having an axial bore characterized by a generally cylindrical interior geometry adjacent the axial bore 322 and terminating in a generally cylindrical interior geometry adjacent the lower opening 324 having a radius smaller than the radius characterizing the axial bore at the axial bore 322. Prior to terminating in the cylindrical geometry at the lower opening 324, the axial bore is characterized by a spherical concave surface geometry along the lower chamber surfaces 37. The body interior surface 126 progresses from an essentially cylindrical surface adjacent the body axial bore 322 and smoothly transitions through a hemi-concave surface along the body lower chamber surfaces 37 tracing out approximately 45 degrees and transitions to an essentially cylindrical surface adjacent the body lower opening 324, the radius of the cylindrical surface adjacent the body lower opening 324 being smaller than the radius of the cylindrical surface adjacent the body axial bore 322.

The bushing 40/140 is characterized by an exterior surface 555 that assumes a generally cylindrical geometry adjacent the upper end 547 and smoothly transitions to a torus-like concave geometry along the lower exterior surface portion 555 and adjacent the lower end portion 546. As the bushing 40/140 is urged downward through the polyaxial bone fixation assembly 100I/200I and the lower exterior surface portion 555 bears against the lower chamber surfaces 37 of the body 20/120, the interior cavity 551 is crush locked around the head of the bone anchor as the flexible arms 545 are drawn together and the position and angulation of the bone anchor is locked with respect to the body 20/120 and the polyaxial bone fixation assembly 100I/200I. The dark arrows show in FIG. 13 illustrate a point of contact between the body 20/120 and the bushing 40/140 when in the locked state.

FIG. 14 illustrates a polyaxial bone fixation assembly 100J/200J that includes a body 20/120 having an axial bore characterized by a generally cylindrical interior geometry adjacent the axial bore 422 and characterized by a torus-like concave interior geometry along the lower chamber surfaces 37 adjacent the lower opening 424. More specifically, the lower chamber surfaces 37 progresses from an essentially cylindrical surface adjacent the body axial bore 422 and transitions through a hemi-concave surface tracing out approximately 45 degrees and smoothly inflects to a hemi-concave surface tracing out approximately 45 degrees adjacent the body lower opening 424.

The bushing 40/140 is characterized by an exterior surface 255 that assumes a generally cylindrical geometry adjacent the upper end 47 and smoothly transitions to a spherical concave geometry or hemi-concave surface along the lower exterior surface portion 255 and adjacent to the lower end portion 246. As the bushing 40/140 is urged downward through the polyaxial bone fixation assembly 100 and the lower exterior surface portion 255 bears against the lower chamber surfaces 37 of the body 20/120, the interior cavity 251 is crush locked around the head of the bone anchor as the flexible arms 245 are drawn together and the position and angulation of the bone anchor is locked with respect to the body 20/120 and polyaxial bone fixation assembly 100J/200J. The dark arrows show in FIG. 14 illustrate a point of contact between the body 20/120 and the bushing 40/140 when in the locked state.

FIGS. 15A-15B illustrate a polyaxial bone fixation assembly 100K/200K that includes a body 20/120 having an axial bore characterized by a generally cylindrical interior geometry adjacent the axial bore 422 and characterized by a torus-like concave interior geometry at the lower chamber surfaces 37 adjacent the lower end 524. More specifically, the body interior surface 126 progresses from an essentially cylindrical surface adjacent the body axial bore 422 and transitions through a hemi-concave surface tracing out approximately 45 degrees and smoothly inflects to a hemi-concave surface tracing out approximately 45 degrees adjacent the body lower opening 524.

The bushing 40/140 is characterized by an exterior surface 355 that assumes a generally cylindrical geometry adjacent the upper end 47 and smoothly transitions to a torus-like concave geometry or hemi-concave surface along the lower exterior surface portion 355 and adjacent to the lower end portion 346. As the bushing is urged downward through the polyaxial bone fixation assembly 100K/200K and the lower exterior surface portion 355 bears against the lower chamber surfaces 37 of the body 20/120, the interior cavity 351 is crush locked around the head of the bone anchor as the flexible arms 45 are drawn together and the position and angulation of the bone anchor is locked with respect to the body 20/120 and polyaxial bone fixation assembly 100K/200K. The dark arrows show in FIGS. 15A and 15B illustrate a point of contact between the body 20/120 and the bushing 40/140 when in the locked state.

FIGS. 16A-16B illustrate a polyaxial bone fixation assembly 100L/200L that includes a body 20/120 having an axial bore characterized by a generally cylindrical interior geometry adjacent the axial bore 422 and characterized by a torus-like concave interior geometry at the lower chamber surfaces 37 adjacent the lower opening 524. More specifically, the body interior surface 126 progresses from an essentially cylindrical surface adjacent the body axial bore 422 and transitions through a hemi-concave surface tracing out approximately 45 degrees and smoothly inflects to a partially-concave surface tracing out approximately degrees adjacent the body lower opening 524.

The bushing 40/140 is characterized by an exterior surface 555 that assumes a generally cylindrical geometry adjacent the upper end 47 and smoothly transitions to a torus-like concave geometry along the lower exterior surface portion 555 and adjacent the lower end portion 546. As the bushing 40/140 is urged downward through the polyaxial bone fixation assembly 100 and the lower exterior surface portion 555 bears against the lower chamber surfaces 37 of the body 20/120, the interior cavity 551 is crush locked around the head of the bone anchor as the flexible arms 545 are drawn together and the position and angulation of the bone anchor is locked with respect to the body 20/120 and the polyaxial bone fixation assembly 100. The dark arrows show in FIGS. 16A and 16B illustrate a point of contact between the body 20/120 and the bushing 40/140 when in the locked state.

Thus, as described above, in the first and second embodiments of FIGS. 1 and 2, the interaction of the bone anchor, bushing and body have specifically designed sections thereof that come into contact to secure the bone anchor within the bushing, as described in FIGS. 5-16. In FIGS. 17 and 18, the interaction of the bone anchor and the bushing involves the head of the bone anchor deflecting the bushing as the head is inserted into the bushing. The arms of the bushing deflect outwardly as the head is inserted and then inwardly as the head is received within the bushing to secure the head therein.

Referring now to FIGS. 17A and 18A, there is illustrated a third embodiment of bone anchor or bone fixation assembly 1700 that generally includes a bone anchor 10 (e.g., a bone screw), a body 1720, a bushing 1740, and a locking cap 92. In the implementation of FIG. 17A, the bushing 1740 has a size and configuration to create an interference fit between the bushing 1740 and the bone anchor 10, whereas in the implementation of FIGS. 1A-1D the bushing 40 include a cavity 51 that is shaped and sized to engage and secure the head 14 when pushing is locked into place. As in the above, the anchor assembly 1700 enables in-situ assembly of the bone anchor 10 to the body 1720 of the anchor assembly 1700 such that the bone anchor 10 may be secured to a patients vertebra prior to being received within the body 1720. Aspects of the anchor assembly 1700 that are similar to the anchor assembly 100 are not repeated below.

The bushing 1740 may be movably positionable within the body 20 between a first (unloaded/unlocked) position where the bone anchor 10 can be connected to or unconnected from the bushing 1740, and a second (loaded/locked) position where the bone anchor 10 is locked with respect to the bushing 1740. The bushing 1740 defines slots, as in FIGS. 1 and 2, that define a plurality of flexible arms 1745 that pivot about a point 1753 (FIG. 18A). The slots may extend from the lower end 1746, the upper end 1747 or both ends 1746, 1747.

To interconnect or attach the bone anchor 10 to the body 1720, the body 1720 may be provided with the bushing 1740 pre-assembled and in the loading position, in which a lower tooth 1741a of an upper portion of the bushing 1740 engages a tooth 1741c of the body in the locking mechanism 1738. The head 14 of the bone anchor 10 is inserted into the lower opening 1724 of the body 1720 and into the interior cavity 1751 of the bushing 1740. As the head 14 is further inserted into the interior cavity 1751 of the bushing 1740 such that the flexible arms 1745 initially pivot outwardly about the point 1753 and then back inwardly until it the head 14 engages the interior surfaces of flexible arms 1745 that pivot about the point 1753 of the bushing 1740 (see FIG. 18A). Thus, the head 14 is "clicked-in" to the bushing 40 as the flexible arms 45 retain the head 14 within the cavity 1751.

After the head 14 of the bone anchor 10 is fully inserted into the cavity 1751 of the bushing 1740, the bushing 1740 is moved down into the lower chamber of the body 1720 to prevent the head 14 of the bone anchor 10 from becoming dislodged from bushing 1740. The downward movement causes the upper portion of the bushing 1740 to be retained within the body 1720 by the interaction of the tooth 1741b engaging the tooth 1741c of the body 1720. When the bone anchor 10 is in the locked position the head 14 is able to rotate polyaxially within the cavity 1751, and thus about the body 20. As illustrated, the bushing 40 of the first implementation, provides for approximately 25° of angulation in any direction with respect to the longitudinal axis 1732. As illustrated, the neck portion 16 acts as a stop when the neck portion 16 contacts the lower and of the bushing 1740.

Referring to FIGS. 17B and 18B, there is illustrated a fourth embodiment of a bone anchor or bone fixation assembly 1800 that generally includes a bone anchor 10 (e.g., a bone screw), a body 1820, a bushing 1840, and a locking cap 92. In the implementation of FIG. 17B, the bushing 1840 has a size and configuration to create an interference fit between the bushing 1840 and the bone anchor 10, whereas in the implementation of FIGS. 2A-2E the bushing 140 include a cavity 151 that is shaped and sized to engage and secure the head 14 when pushing is locked into place. As shown in FIGS. 17B and 18B, the bushing 1840 is sized and configured such that it may be inserted into the body 1820 through the upper opening, but is prevented from exiting through the lower opening.

Referring again to FIGS. 17B and 18B, once the bushing 1840 is placed and assembled into the body 1820, the bushing 1840 may be retainable within the body 1820 by a saddle 1869. For example, after the bushing 1840 is positioned, the saddle 1869 may be inserted into the upper opening 1823 such that a lower surface 1873 of the saddle 1869 contacts an upper surface 1872 of the bushing 1840. As such, the bushing 1840 is retained within the lower chamber 1836 of the body 1820.

The bushing 1840 is movably positionable within the body 1820 between a first position where the bone anchor 10 can be connected to or unconnected from the bushing 1840, and a second position where the bushing 1840 is locked with respect to the bone anchor 10. The lower end portion 1836 of the bushing 1840 preferably includes an interior cavity 1851 for receiving and securing the head 14 of the bone anchor 10 so that the bone anchor 10 can rotate polyaxially through a range of angles with respect to the bushing 1840 and hence with respect to the body 1820 when in an unlocked or loading/unloading position.

To interconnect or attach the bone anchor 10 to the body 1820, the body 1820 may be provided with the bushing 1840 pre-assembled and in the loading position, in which a lower tooth 1841a of the saddle 1869 engages a tooth 1841c of the body in the locking mechanism 1838. The lower surface 1873 of the saddle 1869 contacts the upper surface 1872 of the bushing 1840. The head 14 of the bone anchor 10 is inserted into the lower opening 1824 of the body 1820 and into the interior cavity 1851 of the bushing 1840. As shown in FIG. 18B, the head 14 is further inserted into the interior cavity 1851 of the bushing 1840, the flexible arms 1845 initially pivot outwardly about the point 1853 and then back inwardly until it the head 14 engages the interior surfaces of flexible arms 1845 that pivot about a point 1853 of the bushing 1840. Thus, the head 14 is "snapped-in" to the bushing 1840 as the flexible arms 1845 frictionally retain the head 14 within the cavity 1851.

When the bone anchor 10 is in the locked position the head 14 is rotatable within the cavity 1851. The bushing 140 of the fourth implementation, provides for approximately 41° of angulation in each direction with respect to the longitudinal axis 32, as both the head 14 and the bushing 1841 are rotatable within the lower chamber 1836 of the body 1820.

While the foregoing description and drawings represent the preferred embodiment of the present disclosure, it will be understood that various additions, modifications, combinations and/or substitutions may be made therein without departing from the spirit and scope of the present disclosure as defined in the accompanying claims. In particular, it will be clear to those skilled in the art that the present disclosure may be embodied in other specific forms, structures, arrangements, proportions, and with other elements, materials, and components, without departing from the spirit or essential characteristics thereof. One skilled in the art will appreciate that the invention may be used with many modifications of structure, arrangement, proportions, materials, and components and otherwise, used in the practice of the disclosure, which are particularly adapted to specific environments and operative requirements without departing from the principles of the present disclosure. In addition, features described herein may be used singularly or in combination with other features. The presently disclosed embodiments are, therefore, to be considered in all respects as illustrative and not restrictive, the scope of the disclosure being indicated by the appended claims and not limited to the foregoing description.

It will be appreciated by those skilled in the art that changes could be made to the embodiments described above without departing from the broad inventive concept thereof. It is understood, therefore, that this invention is not limited to the particular embodiments disclosed, but it is intended to cover modifications within the spirit and scope of the present disclosure, as defined by the appended claims.

The invention claimed is:

1. A bone anchor assembly comprising:
   a body having an upper opening located at an upper end of the body and a lower opening located at a lower end of the body, the lower opening sized and configured to receive a head of a bone anchor, a bore extending between the upper and lower openings of the body, wherein the bore defines a lower chamber surface within the body, the body further defining a rod receiving channel extending through a side wall of the body;
   a bushing received within the bore of the body, the bushing including an upper opening located at an upper end of the bushing and a lower opening located at a lower end of the bushing, a bore extending between the upper and lower openings of the bushing, an interior cavity located within the bore of the bushing for receiving at least a portion of a head of a bone anchor, a slot extending from the lower end, the slot permitting a portion of the bushing to expand and collapse about a head of a bone anchor, wherein the expanding and collapsing portion is configured for positioning in direct contact with the lower chamber surface and the head of the anchor;
   a saddle received within a portion of the bore of the body between the bushing and the upper opening of the body, the saddle including a locking mechanism for engaging a corresponding locking mechanism of the bore of the body.

2. The bone anchor assembly of claim 1, wherein the bushing is movable between a locked and unlocked position,
   wherein in the unlocked position a bone anchor can be connected or unconnected from the bushing via the lower opening of the bushing and the portion of the bushing is expandable about the head of the bone anchor,
   wherein in the locked position the portion of the bushing is collapsed about the head of a bone anchor received within the inner cavity such that a position of the bone anchor is locked with respect to the bushing.

3. The bone anchor assembly of claim 2, wherein movement of an instrument, received within the bone anchor assembly, moves the bushing between the unlocked and locked position and moves the saddle between an unlocked and a locked position.

4. The bone anchor assembly of claim 2, wherein the bone anchor is frictionally retained within the inner cavity when the bushing is in the unlocked position.

5. The bone anchor assembly of claim 1,
   wherein downward movement of the saddle within the bore of the body causes a lower surface of the saddle to engage an upper surface of the bushing to move the bushing into the locked position, and in the locked position a lower surface of the bushing contacts the lower chamber surface of the body securing the bushing within the body.

6. The bone anchor assembly of claim 1, wherein the locking mechanism of the saddle and the locking mechanism of the body include corresponding ratchet teeth,
   wherein the corresponding ratchet teeth limit movement of the saddle within the body in a direction along a longitudinal axis of the saddle.

7. The bone anchor assembly of claim 1, wherein the bore extending within the body includes a torus-like convex surface proximate the lower opening of the body.

8. The bone anchor assembly of claim 1, wherein the bore of the body proximate the upper opening of the body defines a first diameter and the bore of the body proximate the lower opening of the body defines a second diameter smaller than the first diameter.

9. The bone anchor assembly of claim 8, wherein the bushing is sized and configured to be inserted into the body through the upper opening,
   wherein the bushing is sized and configured to be inserted into the body through the lower opening when in a rotated state such that a longitudinal axis of the bushing is perpendicular to a longitudinal axis of the body, and
   wherein the bushing is sized and configured such that it is prevented from exiting through the lower opening of the body when in a non-rotated state when the longitudinal axis of the bushing is parallel with the longitudinal axis of the body.

10. The bone anchor assembly of claim 1, wherein the bushing provides for polyaxial movement of a bone anchor operatively coupled with the bushing in both the locked and unlocked position,
    wherein the bushing provides for at least 40-degrees of angulation of a bone anchor in any direction with respect to a longitudinal axis of the bone anchor assembly, when the bone anchor is operatively coupled to the bushing in both the locked and unlocked position.

11. The bone anchor assembly of claim 1, further including:
    a bone anchor including:
       a head sized and configured to be movably received within the interior cavity of the bushing; and
       an externally threaded shaft extending from the head for engaging a patient's bone.

12. The bone anchor assembly of claim 11, wherein the bone anchor further includes a neck located between the head and the externally threaded shaft, the neck having a diameter less than a diameter of the externally threaded shaft,
    wherein polyaxial movement of the bone anchor is limited when the neck comes into contact with the bushing proximate the lower opening.

13. The bone anchor assembly of claim 1, wherein the expanding and collapsing portion is urged radially inward toward the bone anchor by the lower chamber surface of the body.

14. The bone anchor assembly of claim 1, further comprising a locking cap assembly received within the bore of the body to retain a spinal rod within the rod receiving channel.

* * * * *